United States Patent
Araki et al.

(10) Patent No.: US 9,493,814 B2
(45) Date of Patent: Nov. 15, 2016

(54) FLAVIN-BINDING GLUCOSE DEHYDROGENASE HAVING IMPROVED SUBSTRATE SPECIFICITY

(71) Applicant: KIKKOMAN CORPORATION, Noda-shi, Chiba (JP)

(72) Inventors: Yasuko Araki, Noda (JP); Atsushi Ichiyanagi, Noda (JP); Keiichi Ichikawa, Noda (JP); Kozo Hirokawa, Noda (JP)

(73) Assignee: KIKKOMAN CORPORATION, Noda-Shi, Chiba (JP)

(*) Notice: Subject to any disclaimer, the term of this patent is extended or adjusted under 35 U.S.C. 154(b) by 0 days.

(21) Appl. No.: 14/355,326

(22) PCT Filed: Nov. 1, 2012

(86) PCT No.: PCT/JP2012/078283
§ 371 (c)(1),
(2) Date: Apr. 30, 2014

(87) PCT Pub. No.: WO2013/065770
PCT Pub. Date: May 10, 2013

(65) Prior Publication Data
US 2014/0302542 A1 Oct. 9, 2014

(30) Foreign Application Priority Data
Nov. 2, 2011 (JP) .................................. 2011-240934

(51) Int. Cl.
| C12Q 1/54 | (2006.01) |
|---|---|
| C12N 9/04 | (2006.01) |
| C12Q 1/32 | (2006.01) |
| C12Q 1/00 | (2006.01) |

(52) U.S. Cl.
CPC ............... *C12Q 1/54* (2013.01); *C12N 9/0006* (2013.01); *C12Q 1/006* (2013.01); *C12Q 1/32* (2013.01)

(58) Field of Classification Search
None
See application file for complete search history.

(56) References Cited

U.S. PATENT DOCUMENTS

| 7,741,100 | B2 | 6/2010 | Kitabayashi et al. |
|---|---|---|---|
| 8,445,246 | B2 | 5/2013 | Tajima et al. |
| 9,074,239 | B2 | 7/2015 | Tajima et al. |
| 2006/0063217 | A1 | 3/2006 | Omura et al. |
| 2008/0003628 | A1 | 1/2008 | Kitabayashi et al. |
| 2008/0090278 | A1 | 4/2008 | Kitabayashi et al. |
| 2009/0176262 | A1 | 7/2009 | Omura et al. |
| 2009/0181408 | A1 | 7/2009 | Tanaka et al. |
| 2009/0317848 | A1 | 12/2009 | Kawaminami et al. |
| 2010/0297743 | A1 | 11/2010 | Omura et al. |
| 2010/0323378 | A1 | 12/2010 | Honda et al. |
| 2011/0045513 | A1 | 2/2011 | Takenaka et al. |
| 2011/0053194 | A1 | 3/2011 | Yuuki et al. |
| 2011/0318810 | A1 | 12/2011 | Tajima et al. |
| 2013/0309750 | A1 | 11/2013 | Tajima et al. |
| 2014/0057331 | A1 | 2/2014 | Tajima et al. |

FOREIGN PATENT DOCUMENTS

| EP | 1862543 A1 | 12/2007 |
|---|---|---|
| EP | 2241621 A1 | 10/2010 |
| EP | 2508600 A | 10/2010 |
| EP | 2 083 074 B1 | 1/2011 |
| JP | 2005176602 A | 7/2005 |
| JP | 2007-289148 A | 11/2007 |
| JP | 2008-154574 A | 7/2008 |
| JP | 2008-237210 A | 10/2008 |
| JP | 2010-035448 A | 2/2010 |
| JP | 4494978 B2 | 6/2010 |
| JP | 2010-269056 A | 12/2010 |
| JP | 4648993 B2 | 3/2011 |
| JP | 2011-115156 A | 6/2011 |
| WO | WO 2004/058958 A1 | 7/2004 |
| WO | WO 2006/101239 A1 | 9/2006 |
| WO | WO 2007/139013 A1 | 12/2007 |
| WO | WO 2009/069381 A1 | 6/2009 |
| WO | WO 2009/084616 A1 | 7/2009 |
| WO | WO 2010/140431 A1 | 12/2010 |
| WO | WO 2011/004654 A1 | 1/2011 |
| WO | WO 2011/068050 A1 | 6/2011 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Yamaoka et al., Site Directed Mutagenesis Studies of FAD-dependent Glucose Dehydrogenase Catalytic Subunit of Burkholderia Cepacia, Biotechnol. Lett., Nov. 2008, 30(11), pp. 1967-1972.
International Search Report mailed Nov. 27, 2014 for PCT/JP2012/078283.
U.S. Appl. No. 14/124,559, filed Dec. 6, 2013.
*Pharmaceuticals and Medical Devices Safety Information*, No. 206 (Oct. 2004) with English translation.
Tchan-Gi Bak et al., "Studies on the Glucose Dehydrogenase *Aspergillus oryzae*", Biochim. Biophys. Acta, 139, pp. 265-276 (1967).
Tchan-Gi Bak, "Studies on the Glucose Dehydrogenase *Aspergillus oryzae*", Biochim. Biophys. Acta, 139, pp. 277-293 (1967).
Tchan-Gi Bak, "Studies on the Glucose Dehydrogenase *Aspergillus oryzae*", Biochim. Biophys. Acta, 139, pp. 317-327 (1967).

(Continued)

*Primary Examiner* — Christian Fronda
(74) *Attorney, Agent, or Firm* — Holtz, Holtz & Volek PC

(57) ABSTRACT

A flavin-binding glucose dehydrogenase having high substrate specificity for D-glucose and decreased reactivity to D-xylose and/or maltose. More specifically, a flavin-binding glucose dehydrogenase having one or more amino acid substitutions at a position corresponding to position 78, position 79, position 81, position 121, position 122, position 123, position 569 and position 612 of Mucor-derived flavin-binding glucose dehydrogenase. The flavin-binding glucose dehydrogenase enables D-glucose to be measured accurately without being susceptible to the effects of the presence of D-xylose and/or maltose, even under conditions of mounting a large amount of an enzyme such as in glucose sensors.

9 Claims, 4 Drawing Sheets

(56) References Cited

OTHER PUBLICATIONS

Tchan-Gi Bak et al., "Studies on the Glucose Dehydrogenase *Aspergillus oryzae*", Biochim. Biophys. Acta, 139, pp. 328-335 (1967).
Glucose dehydrogenase [Flavin] (2005, updated) http://www.uniprot.org/uniprot/P18172, pp. 1-9.
SEQ-Align (2015) pp. 1-2.
SEQ-Align III (2015) pp. 1-2.
SEQ-Align II (2015) pp. 1-2.
Krasney, et al., "Evolution of the Glucose Dehydrogenase Gene in Drosophila", Mol. Biol. Evol., vol. 7, pp. 155-177.
English-language International Preliminary Report on Patentability and Written Opinion of the International Searching Authority, dated May 6, 2014 for International Application PCT/JP2012/078283 filed Nov. 1, 2012; Applicant: Kikkoman Corporation.
Branden, et al., Introduction to Protein Structure, Garland Publishing Inc., New York, p. 247, 1991.
Krasney, et al., "Evolution of the Glucose Dehydrogenase Gene in Drosophila", Mol. Biol. Evol., vol. 7, 1990, pp. 155-177.

* cited by examiner

Fig. 1

```
                  10        20        30        40        50        60
            ....|....|....|....|....|....|....|....|....|....|....|....|
MpGDH   1   MKITAAIITVATAFASFASAQQDTNSSSTDTYDYVIVGGGVAGLALASRISENKDVTVAV 60
1gpe    1   --------YLPAQQIDVQSSLLSDPSKVAGKTYDYIIAGGGLTGLTVAAKLTENPKIKVLV 53
             *  :   :*  .*.,.  : .****:*.***::**:*:::** ..:.* *

70        80        90       100       110       120
            ....|....|....|....|....|....|....|....|....|....|....|....|
MpGDH   61  LESGPN-ANDRFVVYAPGMYGQAVGTDLCPLIPTTPQENMGNRSLTIATGRLLGGGSAIN 119
1gpe    54  IEKGFYESNDGAIIEDPNAYGQIFGTTVDQNYLTVP--LINNRTNNIKAGKGLGGSTLIN 111
            :*.*   :**   ::   *. *** .** :    *.*   :.**: .* :*: ***.: **

130       140       150       160       170       180
            ....|....|....|....|....|....|....|....|....|....|....|....|
MpGDH   120 GLVWTRGGLKDYDAWEELG-NPGWNGANLFKYFKKVENFTPPTPAQIEYGATYQKSAHGK 178
1gpe    112 GDSWTRPDKVQIDSWEKVFGWEGWNWDNMFEYWKKAEAARTPTAAQLAAGHSFNATCHGT 171
            *  ***  .  : *:**::    ***  *:*:*:**.*   .**.**:  *  ::: :.**.

190       200       210       220       230       240
            ....|....|....|....|....|....|....|....|....|....|....|....|
MpGDH   179 KGPIDVSFTNYEFSQSASWNASLETLDFTALP---DILNGTLAGYSTTPNILDPETVQRV 235
1gpe    172 NGTVQSGARDNGQPWSPIMKALWNTVSALGYPVQQDFLCGHPRGVSMIMNNLD-ENQVRV 230
            :*.::  .    : .*. .*  :* :*:,. .:*   *:*  *  * ** *,  **

250       260       270       280       290       300
            ....|....|....|....|....|....|....|....|....|....|....|....|
MpGDH   236 DSYTGYIAPYTSRNNLNVLANHTVSRIQFAPKNGSEPLKATGVEWYPTGNKNQKQIIKAR 295
1gpe    231 DAARAWLLPNYQRSNLEILTGQWVGKVLFKQTASGP-QAVGVNFG--TNKAVNFDVFAK 286
            *:  .:: * .*.**::*:,: *.:: *  ,...  :*.**::    **  :  : *:

310       320       330       340       350       360
            ....|....|....|....|....|....|....|....|....|....|....|....|
MpGDH   296 YEVIISSGAIGSPKLLEISGIGNKDIVSAAGVESLIDLPGVGSNMQDHVHAITVSTTNIT 355
1gpe    287 HEVLLAAGSAISPLILEYSGIGLKSVLDQANVTQLLDLP-VGINMQDQTTTTVSSRASSA 345
            :**::::*:  ** :** ****  *.::. *.*  ,*:*** ** ****:.   :  * :. :

370       380       390       400       410       420
            ....|....|....|....|....|....|....|....|....|....|....|....|
MpGDH   356 GYTTNSVFVNETLAQEQREEYEANKTGIWATTPNNLGYPTPEQLFNGTEFVSGKEFADKI 415
1gpe    346 GAGQ------------------------------------GQAVFFANFTETFGDYAPQARDLL 373
            *                                        * ..  *.* .  . :  *:

430       440       450       460       470       480
            ....|....|....|....|....|....|....|....|....|....|....|....|
MpGDH   416 RNSTDEWANYYASTN-ASNVELLKKQYAIVASRYEENYLSPIEINFTPGYEGSNVDLQN 474
1gpe    374 NTKLDQWAEEETVARGGFHNVTALKVQYENYRNWLLDEDVAFAELFMDT--EGKINFDLWD 431
            ,,, *:**:  .: ,   **  ** **   , ::  ::  *: :  .  **. *.** :

490       500       510       520       530       540
            ....|....|....|....|....|....|....|....|....|....|....|....|
MpGDH   475 NKYQTVMHVLIAPLSRGYTHINSSDVEDHSVIN-PQYYSHPMDIDVHIASTKLAREIITA 533
1gpe    431 ----------LIPFTRGSVHILSSDPYLWQFANDPKFFLNEFDLLGQAAASKLARDLTSQ 481
                      : *:** .** ***   ,, * *::: : :*:   *:*:****:: :

550       560       570       580       590       600
            ....|....|....|....|....|....|....|....|....|....|....|....|
MpGDH   534 SPGLGDINSGEIEPGMNITSEDDLRSWLS---NNVRSDWHPVGTCAMLPKELGGVVSPAL 590
1gpe    482 G-AMKEYFAGETLPGYNLVQNATLSQWSDYVLQNFRPNWHAVSSCSMMSRELGGVVDATA 540
            . :: : :** ** **:,,: *.* ,   :*,*,:**.*,:***:*:,.:******..:

610       620       630       640       650
            ....|....|....|....|....|....|....|....|....|....|....|
MpGDH   591 MVYGTSNLRVVDASIMPLEVSSHLMQPTYGIAEKAADIIKNFYKTQHKNQN 641
1gpe    541 KVYGTQGLRVIDGSIPPTQVSSHVMTIFYGMALKVADAILDDYAKSA---- 587
            ****.,***:*.** *   :***:*.  **:* **.***::  * ..
```

FLAVIN-BINDING GLUCOSE DEHYDROGENASE HAVING IMPROVED SUBSTRATE SPECIFICITY

CROSS-REFERENCE TO RELATED APPLICATION

This application is a United States national phase application of International Application PCT/JP2012/078283 filed on Nov. 1, 2012.

TECHNICAL FIELD

The present invention relates to a flavin-binding glucose dehydrogenase having improved substrate specificity, a gene and a recombinant DNA thereof, and a method for producing flavin-binding glucose dehydrogenase having improved substrate specificity.

BACKGROUND ART

Blood glucose concentration (blood sugar level) is an important marker for diabetes. Devices for self-monitoring of blood glucose (SMBG) using electrochemical biosensors are widely used by diabetes patients as a device for monitoring their own blood sugar levels. The biosensors used in SMBG devices have conventionally used an enzyme such as glucose oxidase (GOD) that uses glucose as a substrate. However, since GOD has the characteristic of using oxygen as an electron acceptor, SMBG devices using GOD have the potential for preventing the obtaining of accurate measured values due to dissolved oxygen in the measurement sample having an effect on measured values.

On the other hand, various types of glucose dehydrogenases (GDH) are known as enzymes that also use glucose as a substrate but do not use oxygen as an electron acceptor. More specifically, a type of GDH that uses nicotinamide adenine dinucleotide (NAD) or nicotinamide adenine dinucleotide phosphate (NADP) as coenzyme (NAD(P)-GDH) and a type of GDH that uses pyrroloquinoline quinone (PQQ) as coenzyme (PQQ-GDH) have been discovered, and these enzymes are used in the biosensors of SMBG devices. However, NAD(P)-GDH lacks enzyme stability while also having the problem of requiring addition of a coenzyme, while PQQ-GDH has low substrate specificity, causing it to act on sugar compounds other than glucose such as maltose, D-galactose or D-xylose, thereby allowing sugar compounds in measurement samples other than glucose to have an effect on measured values, and resulting in the problem of being unable to obtain accurate measured values.

Recently, PQQ-GDH has been reported to act on maltose contained in transfusion solutions when SMBG devices using PQQ-GDH as a biosensor are used by diabetes patients to measure blood sugar levels, causing measured values to be higher than actual blood sugar levels, and occurrences of disorders such as hypoglycemia caused by treatment based on those values have been reported. In addition, similar occurrences have been determined to also be possible in patients undergoing galactose tolerance tests and xylose absorption tests (see, for example, Non-Patent Document 1). In response to this, when the Pharmaceutical and Food Safety Bureau of the Ministry of Health, Labour and Welfare conducted a cross-reactivity study for the purpose of investigating effects on measured blood sugar levels in the case of having added various sugars to a glucose solution, in the case of adding maltose at 600 mg/dL, D-galactose at 300 mg/dL or D-xylose at 200 mg/dL, measured values obtained with a blood glucose monitoring kit using the PQQ-GDH method were indicated to be nearly 2.5 to 3 times higher than actual glucose concentration. Namely, measured values were determined to be made inaccurate by maltose, D-galactose and D-xylose present in measurement samples, thus resulting in a fervent desire to develop a GDH having high substrate specificity enabling specific measurement of glucose without being affected by sugar compounds causing measurement error in this manner.

With the foregoing in view, attention came to be focused on types of GDH that use coenzymes other than those previously described. For example, GDH derived from *Aspergillus oryzae* is reported in Non-Patent Documents 2 to 5, while flavin-binding glucose dehydrogenase that uses flavin adenine dinucleotide (FAD) as a coenzyme (to be referred to as FAD-GDH) is disclosed in Patent Documents 1 to 3.

However, although the aforementioned enzymes demonstrate the property of having low reactivity with respect to one or more types of sugar compounds that are not D-glucose, they do not have the property of having sufficiently low reactivity with respect to any of maltose, D-galactose and D-xylose. In contrast, the applicant found that flavin-binding GDHs isolated from the genus *Mucor* have the superior property of demonstrating sufficiently low reactivity with respect to maltose, D-galactose and D-xylose (see, for example, Patent Document 4). In addition, the use of this GDH was confirmed to enable accurate measurement of D-glucose concentration without being affected by maltose, D-galactose or D-xylose even under conditions in which these sugar compounds are present within a certain concentration range (see, for example, Patent Document 4). This superior substrate specificity is a major characteristic indicating the superiority of these *Mucor*-derived FAD-GDHs in terms of practical use.

On the other hand, continuing efforts are being made to shorten measurement time by further improving measurement sensitivity, further reduce the scale of measurement systems, and reduce the required size of the measurement sample in order to further improve the convenience of self-monitoring of blood glucose. For example, increasing the amount of glucose measurement enzyme mounted on a glucose sensor has been presumed as a means for improving measurement sensitivity. However, under the predicted conditions of such a usage method in which a large amount of enzyme is present, even in the case of using the previously described *Mucor*-derived FAD-GDH, reactivity to maltose and D-xylose present at a certain concentration or higher has been confirmed, albeit at a very low level, thus demonstrating that there continues to be room for improvement with respect to efforts to lower reactivity with respect to sugar compounds other than D-glucose.

A method has been disclosed for obtaining modified FAD-GDH in which reactivity to D-xylose has been lowered by introducing an amino acid substitution into *Aspergillus*-derived FAD-GDH in an attempt to modify existing FAD-GDH for the purpose of improving the substrate specificity of FAD-GDH (see, for example, Patent Documents 5 and 6). However, since *Aspergillus*-derived FAD-GDH has considerably higher reactivity to D-xylose in comparison with naturally-occurring *Mucor*-derived FAD-GDH, substrate specificity is still considered to be inadequate even with the previously disclosed modified *Aspergillus* species-derived FAD-GDH.

PRIOR ART DOCUMENTS

Patent Documents

Patent Document 1: Japanese Unexamined Patent Publication No. 2007-289148
Patent Document 2: Japanese Patent No. 4494978
Patent Document 3: International Publication No. WO 07/139013
Patent Document 4: Japanese Patent No. 4648993
Patent Document 5: Japanese Unexamined Patent Publication No. 2008-237210
Patent Document 6: International Publication No. WO 09/084616

Non-Patent Documents

Non-Patent Document 1: Pharmaceuticals and Medical Devices Safety Information No. 206, October 2004, Pharmaceutical and Food Safety Bureau, Ministry of Health, Labour and Welfare.
Non-Patent Document 2: Studies on the glucose dehydrogenase of *Aspergillus oryzae*: I. Induction of its synthesis by p-benzoquinone and hydroquinone, T. C. Bak and R. Sato, Biochim. Biophys. Acta, 139, 265-276 (1967).
Non-Patent Document 3: Studies on the glucose dehydrogenase of *Aspergillus oryzae*: II. Purification and physical and chemical properties, T. C. Bak, Biochim. Biophys. Acta, 139, 277-293 (1967).
Non-Patent Document 4: Studies on the glucose dehydrogenase of *Aspergillus oryzae*: III. General enzymatic properties, T. C. Bak, Biochim. Biophys. Acta, 146, 317-327 (1967).
Non-Patent Document 5: Studies on the glucose dehydrogenase of *Aspergillus oryzae*: IV. Histidyl residue as an active site, T. C. Bak and R. Sato, Biochim. Biophys. Acta, 146, 328-335 (1967).

DISCLOSURE OF THE INVENTION

Problems to be Solved by the Invention

An object of the present invention is to provide a novel FAD-GDH that has superior specificity for D-glucose, is unlikely to act on sugar compounds other than D-glucose such as D-xylose or maltose, and is unlikely to be affected by these sugar compounds other than D-glucose when they are present when used to measure D-glucose.

Means for Solving the Problems

As a result of conducting extensive studies to solve the aforementioned problems, the inventors of the present invention found that modified FAD-GDHs, obtained by substituting specific amino acids residue in *Mucor*-derived FAD-GDH, demonstrate superior specificity for D-glucose, is unlikely to act on D-xylose or maltose, and is unlikely to be affected by these sugar compounds other than D-glucose when they are present, thereby leading to completion of the present invention.

Namely, the present invention is as described below.

(1) A flavin-binding glucose dehydrogenase having one or more amino acid substitutions at a position corresponding to an amino acid selected from the group consisting of the following (a) to (i) in the amino acid sequence indicated in SEQ ID NO: 1, an amino acid sequence having sequence identity with that amino acid sequence of 90% or more, or an amino acid sequence in which one or several amino acids have been deleted, substituted or added in that amino acid sequence:

(a) position corresponding to methionine at position 78 in the amino acid sequence described in SEQ ID NO: 1,
(b) position corresponding to tyrosine at position 79 in the amino acid sequence described in SEQ ID NO: 1,
(c) position corresponding to glutamine at position 81 in the amino acid sequence described in SEQ ID NO: 1,
(d) position corresponding to leucine at position 121 in the amino acid sequence described in SEQ ID NO: 1,
(e) position corresponding to valine at position 122 in the amino acid sequence described in SEQ ID NO: 1,
(f) position corresponding to tryptophan at position 123 in the amino acid sequence described in SEQ ID NO: 1,
(g) position corresponding to glutamic acid at position 465 in the amino acid sequence described in SEQ ID NO: 1,
(h) position corresponding to tryptophan at position 569 in the amino acid sequence described in SEQ ID NO: 1, and
(i) position corresponding to serine at position 612 in the amino acid sequence described in SEQ ID NO: 1; wherein,
in comparison with prior to carrying out the aforementioned substitution, the ratio of the reactivity to D-xylose to the reactivity to D-glucose (Xyl/Glc (%)) and/or the ratio of the reactivity to maltose to the reactivity to D-glucose (Mal/Glc (%)) is decreased.

(2) The flavin-binding glucose dehydrogenase described in (1) above, having one or more amino acid substitutions selected from the group consisting of the following (j) to (r):

(j) the amino acid at the position corresponding to methionine at position 78 in the amino acid sequence described in SEQ ID NO: 1 is any of glutamic acid, glutamine, cysteine or asparagine,
(k) the amino acid at the position corresponding to tyrosine at position 79 in the amino acid sequence described in SEQ ID NO: 1 is any of phenylalanine or asparagine,
(l) the amino acid at the position corresponding to glutamine at position 81 in the amino acid sequence described in SEQ ID NO: 1 is any of leucine, phenylalanine or asparagine,
(m) the amino acid at the position corresponding to leucine at position 121 in the amino acid sequence described in SEQ ID NO: 1 is any of cysteine or methionine,
(n) the amino acid at the position corresponding to valine at position 122 in the amino acid sequence described in SEQ ID NO: 1 is any of threonine, alanine or cysteine,
(o) the amino acid at the position corresponding to tryptophan at position 123 in the amino acid sequence described in SEQ ID NO: 1 is any of cysteine, phenylalanine, histidine, valine or serine,
(p) the amino acid at the position corresponding to glutamic acid at position 465 in the amino acid sequence described in SEQ ID NO: 1 is any of arginine, aspartic acid or isoleucine,
(q) the amino acid at the position corresponding to tryptophan at position 569 in the amino acid sequence described in SEQ ID NO: 1 is any of phenylalanine or tyrosine, and
(r) the amino acid at the position corresponding to serine at position 612 in the amino acid sequence described in SEQ ID NO: 1 is any of cysteine or threonine.

(3) The flavin-binding glucose dehydrogenase described in (1) above, wherein the amino acid at the position corresponding to the tryptophan residue at position 569 in the amino acid sequence described in SEQ ID NO: 1 is substituted with tyrosine.

(4) The flavin-binding glucose dehydrogenase described in (1) above, wherein the amino acid at the position corresponding to the tryptophan residue at position 123 in the amino acid sequence described in SEQ ID NO: 1 is substituted with phenylalanine or valine.

(5) The flavin-binding glucose dehydrogenase described in (1) above, having the amino acid substitutions of the following (w) to (ai):

(w) the amino acid at the position corresponding to tryptophan at position 569 in the amino acid sequence described in SEQ ID NO: 1 is tyrosine, and the amino acid at the position corresponding to methionine at position 78 is any of glutamic acid or asparagine, (x) the amino acid at the position corresponding to tryptophan at position 569 in the amino acid sequence described in SEQ ID NO: 1 is tyrosine, and the amino acid at the position corresponding to leucine at position 121 is methionine, (y) the amino acid at the position corresponding to tryptophan at position 569 in the amino acid sequence described in SEQ ID NO: 1 is tyrosine, and the amino acid at the position corresponding to valine at position 122 is cysteine, (z) the amino acid at the position corresponding to tryptophan at position 569 in the amino acid sequence described in SEQ ID NO: 1 is tyrosine, and the amino acid at the position corresponding to tryptophan at position 123 is any of phenylalanine or valine, (aa) the amino acid at the position corresponding to tryptophan at position 569 in the amino acid sequence described in SEQ ID NO: 1 is tyrosine, and the amino acid at the position corresponding to serine at position 612 is any of cysteine or threonine, (ab) the amino acid at the position corresponding to tryptophan at position 569 in the amino acid sequence described in SEQ ID NO: 1 is tyrosine, the amino acid at the position corresponding to methionine at position 78 is asparagine, and the amino acid at the position corresponding to serine at position 612 is cysteine, (ac) the amino acid at the position corresponding to tryptophan at position 123 in the amino acid sequence described in SEQ ID NO: 1 is phenylalanine, and the amino acid at the position corresponding to leucine at position 121 is methionine, (ad) the amino acid at the position corresponding to tryptophan at position 123 in the amino acid sequence described in SEQ ID NO: 1 is phenylalanine, and the amino acid at the position corresponding to serine at position 612 is threonine, (ae) the amino acid at the position corresponding to tryptophan at position 123 in the amino acid sequence described in SEQ ID NO: 1 is valine, and the amino acid at the position corresponding to leucine at position 121 is methionine, (af) the amino acid at the position corresponding to valine at position 232 in the amino acid sequence described in SEQ ID NO: 1 is glutamic acid, the amino acid at the position corresponding to threonine at position 387 is alanine, the amino acid at the position corresponding to isoleucine at position 545 is threonine, and the amino acid at the position corresponding to tryptophan at position 569 is tyrosine, (ag) the amino acid at the position corresponding to valine at position 232 in the amino acid sequence described in SEQ ID NO: 1 is glutamic acid, the amino acid at the position corresponding to threonine at position 387 is alanine, the amino acid at the position corresponding to isoleucine at position 545 is threonine, and the amino acid at the position corresponding to serine at position 612 is cysteine, (ah) the amino acid at the position corresponding to valine at position 232 in the amino acid sequence described in SEQ ID NO: 1 is glutamic acid, the amino acid at the position corresponding to threonine at position 387 is alanine, the amino acid at the position corresponding to isoleucine at position 545 is threonine, and the amino acid at the position corresponding to serine at position 612 is threonine, and (ai) the amino acid at the position corresponding to valine at position 232 in the amino acid sequence described in SEQ ID NO: 1 is glutamic acid, the amino acid at the position corresponding to threonine at position 387 is alanine, the amino acid at the position corresponding to glutamic acid at position 465 is aspartic acid, the amino acid at the position corresponding to isoleucine at position 545 is threonine, and the amino acid at the position corresponding to tryptophan at position 569 is tyrosine.

(6) The flavin-binding glucose dehydrogenase described in any of (1) to (5) above, wherein the ratio of reactivity to D-xylose to reactivity to D-glucose (Xyl/Glc (%)) and/or the ratio of reactivity to maltose to reactivity to D-glucose (Mal/Glc (%)) is decreased by 20% or more in comparison with that prior to introduction of the aforementioned substitutions.

(7) A flavin-binding glucose dehydrogenase gene encoding the flavin-binding glucose dehydrogenase described in any of (1) to (6) above.

(8) A recombinant vector containing the flavin-binding glucose dehydrogenase gene described in (7) above.

(9) A host cell containing the recombinant vector described in (8) above.

(10) A method for producing flavin-binding glucose dehydrogenase, comprising the following steps:

(aj) a step for culturing the host cells described in (9) above, (ak) a step for expressing flavin-binding glucose dehydrogenase gene contained in the aforementioned host cells, and (al) a step for isolating flavin-binding glucose dehydrogenase from the aforementioned culture.

(11) A method for measuring glucose using the flavin-binding glucose dehydrogenase described in any of (1) to (6) above.

(12) A glucose assay kit containing the flavin-binding glucose dehydrogenase described in any of (1) to (6) above.

(13) A glucose sensor containing the flavin-binding glucose dehydrogenase described in any of (1) to (6) above.

Effects of the Invention

According to the present invention, FAD-GDH can be provided having superior substrate specificity in which reactivity to D-xylose and/or maltose is decreased.

BRIEF DESCRIPTION OF THE DRAWINGS

FIG. 1 is a diagram showing the results of comparing the amino acid sequences of *Mucor*-derived FAD-GDH and *P. amagasakiense*-derived glucose oxidase aligned using a multiple alignment program.

Figure 2:
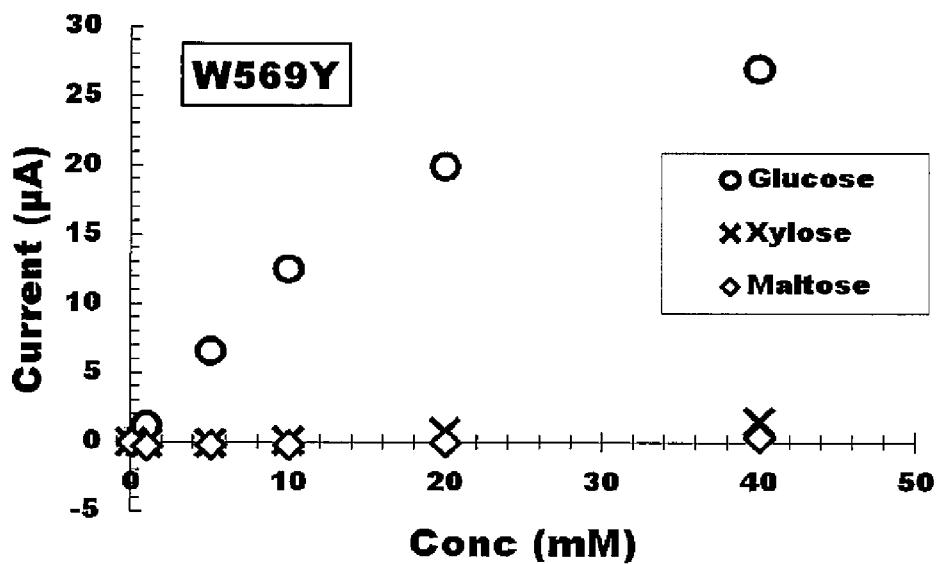
FIG. 2 is a graph showing a plot of current response values versus substrate concentration measured by enzyme electrode assay using modified *Mucor*-derived GDH (W569Y).

BEST MODE FOR CARRYING OUT THE INVENTION (Principle of Action of FAD-GDH of Present Invention and Method for Measuring Activity)

The FAD-GDH of the present invention catalyzes a reaction that forms glucono-δ-lactone by oxidizing a hydroxyl group of glucose in the presence of an electron acceptor in the same manner as known wild-type or mutant FAD-GDH.

Activity of the FAD-GDH of the present invention can be measured with the measuring system indicated below using, for example, phenazine methosulfate (PMS) and 2,6-dichloroindophenol (DCIP) as electron acceptors:

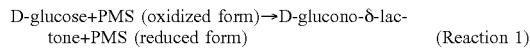

D-glucose+PMS (oxidized form)→D-glucono-δ-lactone+PMS (reduced form)  (Reaction 1)

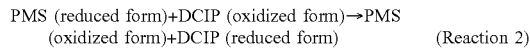

PMS (reduced form)+DCIP (oxidized form)→PMS (oxidized form)+DCIP (reduced form)  (Reaction 2)

More specifically, in Reaction 1, PMS (reduced form) is first formed accompanying oxidation of D-glucose. DCIP is then reduced accompanying oxidation of PMS (reduced form) as the subsequent Reaction 2 proceeds. The degree of consumption of this DCIP (reduced form) can be detected as a change in the amount of absorbance at a wavelength of 600 nm, and enzyme activity can be determined based on this change.

More specifically, the activity of flavin-binding GDH can be measured in accordance with the following procedure. 2.05 mL of 50 mM phosphate buffer (pH 6.5), 0.6 mL of 1 M D-glucose solution and 0.15 mL of 2 mM DCIP solution are mixed followed by warming for 5 minutes at 37° C. Next, 0.1 mL of 15 mM PMS solution and 0.1 mL of enzyme sample solution are added to initiate the reaction. Absorbance is measured at the start of the reaction and over time, and the amount of the decrease in absorbance at 600 nm per minute ($\Delta A600$) as the enzyme reaction proceeds is determined followed by calculating flavin-binding GDH activity in accordance with the following equation. At this time, 1 U of flavin-binding GDH activity is defined as the amount of enzyme that reduces 1 μmol of DCIP in 1 minute in the presence of D-glucose at a concentration of 200 mM at 37° C.

$$\text{GDH activity (U/ml)} = \frac{-(\Delta A600 - \Delta A600_{blank}) \times 3.0 \times df}{16.3 \times 0.1 \times 1.0} \quad \text{[Equation 1]}$$

Furthermore, the value of 3.0 in the equation represents the liquid volume (mL) of the reaction reagents and enzyme sample, the value of 16.3 represents the millimolar molecular extinction coefficient (cm²/μmol) under the activity measurement conditions, the value of 0.1 represents the liquid volume (mL) of the enzyme solution, the value of 1.0 represents the cell path length (cm), $\Delta A600_{blank}$ represents the reduction in absorbance at 600 nm per minute in the case of initiating the reaction by adding 10 mM acetate buffer (pH 5.0) instead of enzyme sample solution, and df represents the dilution factor.

(Amino Acid Sequence of FAD-GDH of Present Invention)

The FAD-GDH of the present invention consists of the amino acid sequence indicated in SEQ ID NO: 1, an amino acid sequence having high sequence identity with that amino acid sequence, such as that having sequence identity of preferably 80% or more, more preferably 85% or more, even more preferably 90% or more, and most preferably 95% or more, or an amino acid sequence in which one or several amino acids in that amino acid sequence have been deleted, substituted or added, and has one or more amino acid substitutions at positions corresponding to amino acids selected from the location equivalent to position 78, the location equivalent to position 79, the location equivalent to position 81, the location equivalent to position 121, the location equivalent to position 122, the location equivalent to position 123, the location equivalent to position 465, the location equivalent to position 569 and the location equivalent to position 612 in the amino acid sequence described in SEQ ID NO: 1.

Preferably, the amino acid substitution at the aforementioned location equivalent to position 78 in the FAD-GDH of the present invention refers to a substitution in which methionine at the location equivalent to position 78 is substituted with any of cysteine, asparagine, glutamic acid or glutamine, the amino acid substitution at the aforementioned location equivalent to position 79 refers to a substitution in which tyrosine at the location equivalent to position 79 is substituted with any of phenylalanine or asparagine, the amino acid substitution at the aforementioned location equivalent to position 81 refers to a substitution in which glutamine at the location equivalent to position 81 is substituted with any of leucine, phenylalanine or asparagine, the amino acid substitution at the aforementioned location equivalent to position 121 refers to a substitution in which leucine at the location equivalent to position 121 is substituted with any of cysteine or methionine, the amino acid substitution at the aforementioned location equivalent to position 122 refers to a substitution in which valine at the location equivalent to position 122 is substituted with any of threonine, alanine or cysteine, the amino acid substitution at the aforementioned location equivalent to position 123 refers to a substitution in which tryptophan at the location equivalent to position 123 is substituted with any of cysteine, phenylalanine, histidine, valine or serine, the amino acid substitution at the aforementioned location equivalent to position 465 refers to a substitution in which glutamic acid at the location equivalent to position 465 is substituted with any of arginine, aspartic acid or isoleucine, the amino acid substitution at the aforementioned location equivalent to position 569 refers to a substitution in which tryptophan at the location equivalent to position 569 is substituted with any of phenylalanine or tyrosine, and the amino acid substitution at the aforementioned location equivalent to position 612 refers to a substitution in which serine at the location equivalent to position 612 is substituted with any of cysteine or threonine.

Among the FAD-GDH of the present invention, a multiple mutant having a plurality of combinations of the aforementioned substitutions is a more preferable example thereof. For example, double mutants having two combinations of the aforementioned substitutions, triple mutants having three combinations, and multiple mutants having multiple combinations of mutations are included in the present invention. Accumulation of such mutations makes it possible to produce an FAD-GDH in which action on D-xylose and/or maltose is further decreased.

In addition, in the production of a multiple mutant as described above, substitutions at locations other than those of the various substitutions listed above can also be combined. The locations of such substitutions have the potential to demonstrate synergistic effects by being introduced in combination with the substitution sites listed above even if prominent effects like those demonstrated by the aforementioned substitution sites are not demonstrated in the case of introducing those substitutions alone.

In addition, mutations that improve thermal stability or known mutations introduced for the purpose of demonstrating different types of effects such as improving resistance to pH or specific substances may also be arbitrarily combined in the FAD-GDH of the present invention in addition to mutations that make it difficult to act on D-xylose and maltose as previously described. Even in the case of having combined such different types of mutations, these FAD-GDHs are included in the present invention provided the effects of the present invention are able to be demonstrated.

For example, an example of a preferable multiple mutant FAD-GDH of the present invention is a mutant in which the amino acid at the position corresponding to tryptophan at position 569 in the amino acid sequence indicated in SEQ ID NO: 1 has been substituted with tyrosine, and another mutation is further combined with this mutation and introduced therein, and specific examples of other mutations include mutations in which the amino acid at the position corresponding to methionine at position 78 is either glutamic acid or asparagine. Alternatively, an example of a preferable multiple mutant FAD-GDH of the present invention is a mutation in which the amino acid at the position corresponding to tryptophan at position 569 in the amino acid sequence described in SEQ ID NO: 1 is tyrosine, and the amino acid at the position corresponding to leucine at position 121 is methionine. Alternatively, an example of a preferable multiple mutant FAD-GDH of the present invention is a mutation in which the amino acid at the position corresponding to tryptophan at position 569 in the amino acid sequence described in SEQ ID NO: 1 is tyrosine, and the amino acid at the position corresponding to valine at position 122 is cysteine. Alternatively, an example of a preferable multiple mutant FAD-GDH of the present invention is a mutation in which the amino acid at the position corresponding to tryptophan at position 569 in the amino acid sequence described in SEQ ID NO: 1 is tyrosine, and the amino acid at the position corresponding to tryptophan at position 123 is phenylalanine or valine. Alternatively, an example of a preferable multiple mutant FAD-GDH of the present invention is a mutation in which the amino acid at the position corresponding to tryptophan at position 569 in the amino acid sequence described in SEQ ID NO: 1 is tyrosine, and the amino acid at the position corresponding to serine at position 612 is either cysteine or threonine. Alternatively, an example of a preferable multiple mutant FAD-GDH of the present invention is a mutation in which the amino acid at the position corresponding to tryptophan at position 569 in the amino acid sequence described in SEQ ID NO: 1 is tyrosine, the amino acid at the position corresponding to methionine at position 78 is asparagine, and the amino acid at the position corresponding to serine at position 612 is cysteine. Alternatively, an example of a preferable multiple mutant FAD-GDH of the present invention is a mutation in which the amino acid at the position corresponding to tryptophan at position 123 in the amino acid sequence described in SEQ ID NO: 1 is phenylalanine, and the amino acid at the position corresponding to leucine at position 121 is methionine. Alternatively, an example of a preferable multiple mutant FAD-GDH of the present invention is a mutation in which the amino acid at the position corresponding to tryptophan at position 123 in the amino acid sequence described in SEQ ID NO: 1 is phenylalanine, and the amino acid at the position corresponding to serine at position 612 is threonine. Alternatively, an example of a preferable multiple mutant FAD-GDH of the present invention is a mutation in which the amino acid at the position corresponding to tryptophan at position 123 in the amino acid sequence described in SEQ ID NO: 1 is valine, and the amino acid at the position corresponding to leucine at position 121 is methionine.

Alternatively, an example of a preferable multiple mutant FAD-GDH of the present invention is a mutation in which the amino acid at the position corresponding to valine at position 232 in the amino acid sequence described in SEQ ID NO: 1 is glutamic acid, the amino acid at the position corresponding to threonine at position 387 is alanine, the amino acid at the position corresponding to isoleucine at position 545 is threonine, and the amino acid at the position corresponding to tryptophan at position 569 is tyrosine. Alternatively, an example of a preferable multiple mutant FAD-GDH of the present invention is a mutation in which the amino acid at the position corresponding to valine at position 232 in the amino acid sequence described in SEQ ID NO: 1 is glutamic acid, the amino acid at the position corresponding to threonine at position 387 is alanine, the amino acid at the position corresponding to isoleucine at position 545 is threonine, and the amino acid at the position corresponding to serine at position 612 is cysteine. Alternatively, an example of a preferable multiple mutant FAD-GDH of the present invention is a mutation in which the amino acid at the position corresponding to valine at position 232 in the amino acid sequence described in SEQ ID NO: 1 is glutamic acid, the amino acid at the position corresponding to threonine at position 387 is alanine, the amino acid at the position corresponding to isoleucine at position 545 is threonine, and the amino acid at the position corresponding to serine at position 612 is threonine. Alternatively, an example of a preferable multiple mutant FAD-GDH of the present invention is a mutation in which the amino acid at the position corresponding to valine at position 232 in the amino acid sequence described in SEQ ID NO: 1 is glutamic acid, the amino acid at the position corresponding to threonine at position 387 is alanine, the amino acid at the position corresponding to glutamic acid at position 465 is aspartic acid, the amino acid at the position corresponding to isoleucine at position 545 is threonine, and the amino acid at the position corresponding to tryptophan at position 569 is tyrosine.

As was previously described hereinbelow, FAD-GDH of the present invention can be obtained by, for example, first acquiring a gene encoding an amino acid sequence that approximates the amino acid sequence of SEQ ID NO: 1 using an arbitrary method, and then introducing an amino acid substitution at any of the locations equivalent to prescribed locations in SEQ ID NO: 1.

Examples of methods used to introduce a target amino acid substitution include a method consisting of randomly introducing a mutation and a method consisting of introducing a site-specific mutation at a presumed site. Examples of the former method include error-prone PCR (Techniques, 1, 11-15 (1989)) and methods using XL1-Red competent cells (Stratagene) that are easily modified by being susceptible to the occurrence of errors in plasmid replication during cell proliferation. In addition, examples of the latter method include a method consisting of introducing a site-specific mutation with, for example, the commercially available Quick Change Site-Directed Mutagenesis Kit (Stratagene) by constructing a three-dimensional structure by crystal structure analysis of a target protein and selecting an amino acid predicted to impart a target effect based on that information. Alternatively, another example of the latter method consists of introducing a site-specific mutation by selecting an amino acid predicted to impart a target effect using the three-dimensional structure of a known protein having a high degree of homology with the target protein.

A "location corresponding to the amino acid sequence of SEQ ID NO: 1" referred to here, for example, refers to the same location in an alignment in the case of having aligned the amino acid sequence of SEQ ID NO: 1 with another amino acid sequence of FAD-GDH having sequence identity with SEQ ID NO: 1 (preferably of 80% or more, more preferably of 85% or more, even more preferably of 90% or more, and most preferably of 95% or more). Furthermore, sequence identity of an amino acid sequence can be calculated by a program such as the maximum matching or search homology program of Genetyx-Mac (Software Development) or by a program such as the maximum matching or multiple alignment program of DNASIS Pro (Hitachi Software).

In addition, an example of a method for specifying a "location corresponding to an amino acid" can be carried out by comparing amino acid sequences using a known algorithm such as the Lipman-Pearson algorithm, and imparting maximum identity to retained amino acid residues present in the amino acid sequence of FAD-GDH. By aligning the amino acid sequences of various types of FAD-GDH using this type of method, the same locations of homologous amino acid residues in each FAD-GDH sequence can be determined irrespective of insertions or deletions in the amino acid sequence. Since "same locations" specified in this manner are thought to be present at the same locations in a three-dimensional structure, they can be assumed to have similar effects with respect to substrate specificity of a target FAD-GDH.

Although various types of variations are presumed to exist in the FAD-GDH of the present invention within the range of the aforementioned sequence identity, all of these can be included in the FAD-GDH of the present invention provided the enzymological properties of these various types of FAD-GDH are similar to those of the FAD-GDH of the present invention described in the present description. FAD-GDH having such amino acid sequences is industrially useful since it has high substrate specificity and is not susceptible to the effects of the presence of a sugar compound other than D-glucose, such as D-xylose or maltose.

In addition, in the FAD-GDH of the present invention, it is important that the amino acid at the aforementioned location equivalent to position 78 be any of cysteine, asparagine, glutamic acid or glutamine, that the amino acid at the location equivalent to position 79 be any of phenylalanine or asparagine, that the amino acid at the location equivalent to position 81 be any of leucine, phenylalanine or asparagine, that the amino acid at the location equivalent to position 121 be any of cysteine or methionine, that the amino acid at the location equivalent to position 122 be any of threonine, alanine or cysteine, that the amino acid at the location equivalent to position 123 be any of cysteine, phenylalanine, histidine, valine or serine, that the amino acid at the location equivalent to position 465 be any of arginine, aspartic acid or isoleucine, that the amino acid at the location equivalent to position 569 be any of phenylalanine or tyrosine, or that the amino acid at the location equivalent to position 612 be any of cysteine or threonine, while it is not important as to whether or not they are the result of an unnatural substitution procedure. For example, in the case of introducing a desired substitution using as a starting material a protein in which amino acids at the aforementioned locations inherently differ from the desired residues of the present invention by using a known technology therein, those desired amino acid residues can be introduced by substitution. On the other hand, in the case of acquiring a desired protein by a known peptide total synthesis, or in the case of synthesizing an entire gene sequence so as to encode a protein having a desired amino acid sequence and then acquiring the desired protein on the basis thereof, or in the case of inherently having a sequence that is found in nature, the FAD-GDH of the present invention can be obtained without having to go through a step of unnatural substitution.

(Improvement of Substrate Specificity of FAD-GDH of Present Invention)

The FAD-GDH of the present invention is characterized by having high substrate specificity. More specifically, the FAD-GDH of the present invention is characterized by having extremely low reactivity with respect to maltose, D-galactose or D-xylose in the same manner as the genus *Mucor*-derived FAD-GDH described in Japanese Patent No. 4648993 previously discovered by the inventors of the present invention. More specifically, reactivity with respect to maltose, D-galactose or D-xylose is 2% or less in each case when based on a value of 100% for reactivity with respect to D-glucose. Since the FAD-GDH used in the present invention has high substrate specificity in this manner, it is capable of accurately measuring the amount of D-glucose even in samples from patients receiving administration of a transfusion solution containing maltose or samples from patients undergoing galactose tolerance tests or xylose tolerance tests without being affected by sugar compounds such as maltose, D-galactose or D-xylose contained in measurement samples. Moreover, since the FAD-GDH of the present invention has even higher substrate specificity for D-glucose than the genus *Mucor*-derived FAD-GDH described in Japanese Patent No. 4648993, it can be expected to demonstrate even greater industrial usefulness.

In addition, the FAD-GDH of the present invention preferably demonstrates extremely low measured values during measurements using sugar compounds such as maltose, D-galactose or D-xylose as substrates instead of D-glucose as previously described, while also preferably enables accurate measurement of D-glucose even under conditions in which there is contamination by sugar compounds such as maltose, D-galactose or D-xylose. More specifically, measured values in the case one or more contaminating sugar compounds selected from maltose, D-galactose or D-xylose are present are preferably 96% to 103%, while measured values in the case three types of contaminating sugar compounds consisting of maltose, D-galactose or D-xylose are simultaneously present are preferably 96% to 104%, based on a value of 100% for the reactivity with respect to D-glucose under conditions in which these contaminating sugar compounds are not present.

In the case of using FAD-GDH having such characteristics, D-glucose levels can be accurately measured even under circumstances in which maltose, D-galactose or D-xylose are present in a measurement sample.

Various enzymological properties possessed by FAD-GDH can be investigated using known techniques for specifying various properties of enzymes, such as by using methods described in the following examples. Various properties of enzymes can also be investigated to a certain degree in a liquid culture of a microorganism that produces various types of FAD-GDH or at an intermediate stage of the purification process, and more specifically, can be investigated using purified enzyme.

The modified FAD-GDH of the present invention is such that the ratio of reactivity to an equimolar concentration of D-xylose to reactivity to D-glucose (Xyl/Glc (%)) and/or the ratio of reactivity to an equimolar concentration of maltose to reactivity to D-glucose (Mal/Glc (%)) under reaction conditions based on the previously described activity measurement method is decreased in comparison with prior to introduction of an amino acid substitution, and is preferably decreased by 20% or more, more preferably by 30% or more, even more preferably by 40% or more, and most preferably by 50% or more.

In the case of the FAD-GDH of the present invention, only one of the ratio of Xyl/Glc (%) or Mal/Glc (%) may be decreased to a preferable degree in comparison with FAD-GDH prior to introduction of an amino acid substitution, or both may be decreased to a preferable degree. The reactivities are more preferably decreased with respect to both substrates.

In addition, since the FAD-GDH of the present invention is an enzyme that inherently has superior substrate specificity for D-glucose as previously described, measured values suggesting the effects of the presence of D-xylose and maltose are presumed to hardly be detected at all during measurement of reactivity carried out using D-xylose and maltose at molar concentrations roughly equal to normal fasting blood sugar levels (≤126 mg/dL (7 mM)). Therefore, when measuring reactivity to D-xylose and maltose with the FAD-GDH of the present invention, measurement is preferably carried out using a large amount of enzyme solution in which reactivity to an equimolar concentration of glucose is 2 U/ml or more, preferably 5 U/ml or more and more preferably 10 U/ml or more under conditions in which D-xylose and/or maltose are present at an excess concentration of, for example, 200 mM. As a result of measuring under such conditions, the effects of contaminants can be examined while presuming conditions similar to those when mounting a large amount of enzyme on a glucose sensor.

Furthermore, since the ratio of reactivity to an equimolar concentration of D-xylose to reactivity to D-glucose (Xyl/Glc (%)) and the ratio of reactivity to an equimolar concentration of maltose to reactivity to D-glucose (Mal/Glc (%)) vary according to the type and culturing conditions of the transformant or the measurement conditions of enzyme activity, it is necessary to compare their respective values before and after introducing an amino acid substitution under the same conditions.

(Examples of Naturally-Occurring FAD-GDH Serving as Source of FAD-GDH of Present Invention)

The FAD-GDH of the present invention can be acquired by using a known protein as a starting material and modifying that protein. In particular, the use of a starting material having numerous similarities with the enzymological properties desired in the FAD-GDH of the present invention is advantageous in terms of acquiring a desired FAD-GDH.

Examples of the aforementioned starting material include known FAD-GDH. Preferable examples of microorganisms derived from known FAD-GDH include microorganisms classified in the subphylum Mucoromycotina, preferably the class Mucoromycetes, more preferably the order Mucorales and even more preferably the family Mucoraceae. Specific examples of preferable starting materials for acquiring the FAD-GDH of the present invention include FAD-GDH derived from the genus *Mucor*, the genus *Absidia* or the genus *Actinomucor*.

Specific examples of preferable microorganisms classified in the genus *Mucor* include *Mucor prainii*, *Mucor javanicus*, *Mucor dimorphosporus* and *Mucor circinelloides* f. *circinelloides*. More specifically, these include *Mucor prainii* NISL0103, *Mucor javanicus* NISL0111 and *Mucor circinelloides* f. *circinelloides* NISL0117. Specific examples of preferable microorganisms belonging to the genus *Absidia* include *Absidia cylindrospora* and *Absidia hyalospora*. More specifically, these include *Absidia cylindrospora* NISL0211 and *Absidia hyalospora* NISL0218. A specific example of preferable microorganism classified in the genus *Actinomucor* is *Actinomucor elegans*. More specifically, this includes *Actinomucor elegans* NISL9082. Furthermore, the aforementioned microbial strains are deposited with the Noda Institute for Scientific Research (NISL), and cultures can be obtained by going through the prescribed procedures.

(Acquisition of Gene Encoding FAD-GDH of Present Invention)

A genetic engineering technique is preferably used to efficiently acquire the FAD-GDH of the present invention. A commonly used gene cloning method is normally used to acquire a gene encoding the FAD-GDH of the present invention (hereinafter to be referred to as FAD-GDH gene). For example, in order to acquire the FAD-GDH of the present invention by using a known FAD-GDH as a starting material and modifying that known FAD-GDH, chromosomal DNA or mRNA can be extracted according to an ordinary method such as the method described in Current Protocols in Molecular Biology (Wiley Interscience, 1989) from known microbial cells or various other cells having the ability to produce FAD-GDH. Moreover, cDNA can also be synthesized using mRNA as a template. A chromosomal DNA or cDNA library can be prepared by using chromosomal DNA or cDNA obtained in this manner.

Next, suitable probe DNA is synthesized based on amino acid sequence information of known FAD-GDH and this is used to select FAD-GDH gene having high substrate specificity from a chromosomal DNA or cDNA library, or DNA containing a target gene fragment encoding FAD-GDH having high substrate specificity is amplified by a suitable polymerase chain reaction (PCR) method such as 5'-RACE or 3'-RACE by preparing suitable primer DNA based on the aforementioned amino acid sequence, after which these DNA fragments are linked to allow the obtaining of DNA containing the full length of the target FAD-GDH gene.

A method consisting of introducing a mutation into a gene encoding a starting material in the form of FAD-GDH, and selecting the FAD-GDH of the present invention having high substrate specificity by using the enzymological properties of the FAD-GDH expressed from various types of mutant genes as an indicator can be employed as a method for acquiring the FAD-GDH of the present invention having high substrate specificity by using a known FAD-GDH as a starting material.

Mutagenic treatment of the FAD-GDH gene used as a starting substance can be carried out by a known arbitrary method corresponding to the intended form of the mutation. Namely, a wide variety of methods can be used, including methods that allow a mutagenic chemical to contact and act on FAD-GDH gene or recombinant DNA incorporating that gene, ultraviolet irradiation methods, genetic engineering techniques and methods utilizing protein engineering techniques.

Examples of mutagenic chemicals used in the aforementioned mutagenic treatment include hydroxylamine, N-methyl-N'-nitro-N-nitrosoguanine, nitrous acid, sulfurous acid, hydrazine, formic acid and 5-bromouracil.

The various conditions under which contact and action are allowed to occur can be determined corresponding to the type of chemical used, and there are no particular limitations thereon provided they are capable of actually inducing a desired mutation in *Mucor*-derived FAD-GDH gene. Normally, a desired mutation can be induced by allowing a mutagenic chemical to contact and act for 10 minutes or more, and preferably for 10 minutes to 180 minutes, at a reaction temperature of 20° C. to 80° C. and at a chemical concentration of preferably 0.5 M to 12 M. In the case of carrying out ultraviolet irradiation as well, irradiation can be carried out in accordance with ordinary methods as previously described (Chemistry Today, p. 24-30, June 1989).

A technique known as site-specific mutagenesis can typically be used as a method that utilizes protein engineering techniques. Examples thereof include the Kramer method (Nucleic Acids Res., 12, 9441 (1984); Methods Enzymol., 154, 350 (1987); Gene 37, 73 (1985)), the Eckstein method (Nucleic Acids Res., 13, 8749 (1985); Nucleic Acids Res., 13, 8765 (1985); Nucleic Acids Res., 14, 9679 (1986)), and the Kunkel method (Proc. Natl. Acad. Sci. U.S.A., 82, 488 (1985); Methods Enzymol., 154, 367 (1987)). Specific examples of methods for transforming base sequences present in DNA include methods using commercially available kits (such as the Transformer Mutagenesis Kit (Clontech), the EXOIII/Mung Bean Deletion Kit (Stratagene), and the Quick Change Site-Directed Mutagenesis Kit (Stratagene).

In addition, a commonly used technique known as the polymerase chain reaction method can also be used (Technique, 1, 11 (1989)).

Furthermore, in addition to the aforementioned gene modification methods, a desired modified FAD-GDH gene having high substrate specificity can be synthesized directly by organic synthesis methods or enzymatic synthesis methods.

In the case of determining or confirming the DNA base sequence of the FAD-GDH gene of the present invention after having been selected according to any of the arbitrary methods described above, a system such as the CEQ2000 Multi Capillary DNA Analysis System (Beckman Coulter) may be used.

(Vector and Host Cells Inserted with FAD-GDH of Present Invention)

The FAD-GDH gene of the present invention obtained in the manner described above can be incorporated into a vector such as a bacteriophage, cosmid or plasmid used in the transformation of prokaryotic or eukaryotic cells followed by transformation or transduction of host cells corresponding to each vector in accordance with ordinary methods.

An example of eukaryotic cells is yeast. Examples of microorganisms classified as yeast include *Zygosaccharomyces* species, *Saccharomyces* species, *Pichia* species and *Candida* species.

The inserted gene may also contain a marker gene for enabling selection of transformed cells. Examples of marker genes include genes such as URA3 or TRP1 that complement the nutrient requirements of the host. In addition, the inserted gene preferably contains a promoter or other control sequence capable of expressing the gene of the present invention in host cells (such as an enhancer sequence, terminator sequence or polyadenylation sequence). Specific examples of promoters include GAL1 promoter and ADH1 promoter. Although known methods such as methods using lithium acetate (Methods Mol. Cell. Biol., 5, 255-269 (1995)) or electroporation (J. Microbiol. Methods, 55 (2003), 481-484) can be preferably used to transform yeast, the method used is not limited thereto, but rather transformation may also be carried out by various arbitrary methods such as the spheroblast method or glass bead method.

In addition, other examples of eukaryotic host cells include mold cells such as *Aspergillus* species or *Trichoderma* species. The inserted gene preferably contains a promoter (such as a tef1 promoter) or other control sequence (such as a secretion signal sequence, enhancer sequence, terminator sequence or polyadenylation sequence) capable of expressing the gene of the present invention in host cells. In addition, the inserted gene may also contain a marker gene such as niaD or pyrG for enabling selection of transformed cells. Moreover, the inserted gene may also contain a homologous recombination region for insertion into an arbitrary chromosome site. A known method such as a method using polyethylene glycol and calcium chloride following the formation of protoplasts (Mol. Gen. Genet., 218, 99-104 (1989)) can be preferably used to transform filamentous fungi.

Examples of prokaryotic host cells include microorganisms belonging to the genus *Escherichia*, such as *E. coli* strain K-12, *E. coli* strain BL21(DE3), *E. coli* strain JM109, *E. coli* strain DH5α, *E. coli* strain W3110 or *E. coli* strain C600 (all of which are available from TakaraBio). Host cells inserted with DNA (transformants) are obtained by transforming or transducing these host cells. An example of a method used to introduce a recombinant vector into host cells consists of introducing recombinant DNA in the presence of calcium ions in the case the host cells are microorganisms belonging to the species *E. coli*. Moreover, electroporation may also be used. Commercially available competent cells (such as ECOS Competent *Escherichia coli* BL21(DE), Nippon Gene) may also be used.

(Production of FAD-GDH of Present Invention)

The FAD-GDH of the present invention may be produced by culturing host cells that produce the FAD-GDH of the present invention acquired in the manner described above, expressing flavin-binding glucose dehydrogenase gene contained in the aforementioned host cells, and then isolating the flavin-binding glucose dehydrogenase from the aforementioned culture.

Although YPD (2% Bacto Peptone, 1% Bacto Yeast Extract and 2% glucose) liquid medium widely used to culture *Saccharomyces cerevisiae*, for example, is thought to be able to be preferably used to culture the aforementioned eukaryotic host cells, other nutrient sources and components may be added either alone or in combination provided the addition thereof is able to improve the produced amount of the flavin-binding GDH used in the present invention.

Examples of carbon sources used in the medium include assimilable carbon compounds such as glucose, starch hydrolysates, glycerin, fructose or molasses. Examples of nitrogen sources include usable nitrogen compounds such as yeast extract, peptones, meat extracts, corn stiplica, soybean powder, malt extract, amino acids, ammonium sulfate or ammonium nitrate. Examples of inorganic substances include various types of salts such as sodium chloride, potassium chloride, magnesium sulfate, manganese chloride, ferrous chloride, monopotassium phosphate, dipotassium phosphate, sodium carbonate or calcium chloride. Vitamins or antifoaming agents and the like may also be added as necessary.

Examples of media used to culture the aforementioned prokaryotic host cells include media obtained by adding one or more types of inorganic salts such as sodium chloride, monopotassium phosphate, dipotassium phosphate, magnesium sulfate, magnesium chloride, ferric chloride, ferric sulfate or manganese sulfate to one or more types of nitrogen sources such as yeast extract, tryptone, peptone, beef extract, corn stiplica or soy bean or wheat bran percolate, followed by suitably adding a sugar source or vitamins and the like as necessary.

Although varying according to the microorganism cultured, culturing conditions can be suitably set by, for example, adjusting the starting pH of the medium to a pH of 5 to 10, setting the culturing temperature to 20° C. to 40° C., and setting the culturing time to 15 hours to 25 hours, 1 day to 2 days, or 3 days to 7 days, and culturing is carried out by deep aeration-agitation culturing, shake culturing or static culturing and the like.

An example of medium and culturing conditions in the case of culturing yeast of the genus *Zygosaccharomyces* consists of shake culturing at 30° C. and 200 rpm for 24 hours using a medium containing 2% Bacto Peptone, 1% Bacto Yeast Extract and 2% glucose. Culturing of *Escherichia coli*, for example, may be carried out by deep aeration-agitation culturing, shake culturing or static culturing at a culturing temperature of 10° C. to 42° C., preferably at a culturing temperature of about 25° C. for 4 hours to 24 hours, and more preferably at a culturing temperature of about 25° C. for 4 to 8 hours.

Following completion of culturing, an ordinary enzyme collection means can be used to collect flavin-binding GDH from within cultured microbial cells.

In the case the aforementioned enzyme is present in microbial cells, the enzyme is preferably collected from the microbial cells by separating the cells by, for example, an operation such as filtration or centrifugal separation. For example, a method consisting of crushing microbial cells using an ordinary crushing means such as an ultrasonic cell crusher, French press or Dyno-Mill, a method consisting of lysing microbial cell walls using a cell wall digesting enzyme such as lysozyme, or a method consisting of extracting enzyme from the microbial cells using a surfactant such as Triton X-100, can be used either alone or in combination.

In the case the aforementioned enzyme is present outside microbial cells, the microbial cells are separated by an operation such as filtration or centrifugal separation followed by recovering the supernatant. Next, insoluble matter is removed by filtration or centrifugal separation and the like to obtain an enzyme extract. In order to isolate the flavin-binding GDH from the resulting extract and purify as necessary, nucleic acid is removed as necessary followed by fractionating the extract by adding ammonium sulfate, alcohol or acetone and the like and collecting the precipitate to allow the obtaining of a crude enzyme of the FAD-GDH of the present invention.

The crude FAD-GDH of the present invention can be further purified by using any arbitrary known means. A sample of the purified FAD-GDH enzyme of the present invention can be obtained by, for example, gel filtration using Sephadex, Ultrogel or Bio-Gel and the like, adsorption and elution using an ion exchange resin, electrophoresis using polyacrylamide gel and the like, an adsorption and elution method using hydroxyapatite, a precipitation method such as sucrose density gradient centrifugation, affinity chromatography, a fractionation method using a molecular sieve film membrane or hollow fiber membrane and the like, or a combination thereof.

(D-Glucose Measurement Method Using FAD-GDH of Present Invention)

The present invention also discloses a glucose assay kit that contains the FAD-GDH of the present invention, and for example, D-glucose present in blood (blood sugar level) can be measured using the FAD-GDH of the present invention by using this glucose assay kit.

The glucose assay kit of the present invention contains FAD-GDH modified according to the present invention in amount at least sufficient for one assay. Typically, the glucose assay kit of the present invention contains, in addition to the modified FAD-GDH of the present invention, a buffer required for assay, a mediator, glucose standard solutions for preparing a calibration curve, and an indicator of use. The FAD-GDH modified according to the present invention can be provided in various forms, such as a freeze-dried reagent or solution in a suitable preservative solution.

In the case of a colorimetry type of glucose assay kit, D-glucose concentration can be measured according to that described below. A liquid or solid composition containing FAD-GDH, electron acceptor and at least one substance in the form of a reaction accelerator selected from the group consisting of N-(2-acetamide)-iminodiacetic acid (ADA), bis(2-hydroxyethyl)iminotris(hydroxymethyl)methane (Bis-Tris), sodium carbonate and imidazole are made to be retained in the reaction layer of the glucose assay kit. Here, a pH buffer and coloring reagent are added as necessary. A sample containing glucose is then added thereto and allowed to react for a fixed period of time. During this time, absorbance is monitored that is equivalent to the maximum absorption wavelength of a pigment able to polymerize and form as a result of electrons being accepted by a discoloring electron acceptor or electron acceptor due to reduction. D-glucose concentration in the sample can be calculated based on the calibration curve preliminarily prepared using standard D-glucose concentration solutions from the rate of change in absorbance per unit time in the case of using a rate method, or from the change in absorbance until the time all of the D-glucose in the sample has been oxidized in the case of using an endpoint method.

D-glucose can be quantified by adding a mediator and coloring reagent able to be used in this method in the form of, for example, 2,6-dichloroindophenol (DCIP) to serve as an electron acceptor, and then monitoring the decrease in absorbance at 600 nm. In addition, D-glucose concentration can be calculated by adding phenazine methosulfate (PMS) as an electron acceptor and further adding nitrotetrazolium blue (NTB) as a coloring reagent, and determining the amount of diformazan formed by measuring absorbance at 570 nm. Furthermore, it goes without saying that the electron acceptor and coloring reagent used are not limited thereto.

(Glucose Sensor Containing FAD-GDH of Present Invention)

The present invention also relates to a glucose sensor that uses the FAD-GDH of the present invention. A carbon electrode, gold electrode or platinum electrode and the like is used as an electrode, and the enzyme of the present invention is immobilized on this electrode. Examples of methods for immobilizing on the electrode include the use of a crosslinking reagent, sealing in a polymer matrix, coating with a dialysis membrane, use of a photostabilized polymer, use of an electrically conductive polymer or use of an oxidation-reduction polymer, the enzyme of the present invention may be immobilized in a polymer or immobilized on an electrode together with an electron mediator typically represented by ferrocene or a derivative thereof, or a combination of these methods may be used. Typically, after immobilizing the modified FAD-GDH of the present invention on a carbon electrode using glutaraldehyde, the glutaraldehyde is blocked by treating with a reagent having amine groups.

Measurement of D-glucose concentration can be carried out in the manner described below. A buffer is placed in a constant temperature cell and maintained at a fixed temperature. Potassium ferricyanide or phenazine methosulfate and the like can be used for the mediator. An electrode immobilized with the modified FAD-GDH of the present invention is used for the working electrode along with using a counter electrode (such as a platinum electrode) and reference electrode (such as an Ag/AgCl electrode). After applying a fixed voltage to the carbon electrode and the current has reached a steady state, a sample containing D-glucose is added followed by measurement of the increase in current. D-glucose concentration in the sample can be calculated according to a calibration curve prepared using D-glucose solutions having standard concentrations.

As a specific example of measurement of glucose concentration, 1.5 U of the FAD-GDH of the present invention are immobilized on a glassy carbon (GC) electrode followed by measuring the current response to D-glucose concentration. 1.8 ml of potassium phosphate buffer (pH 6.0) and 0.2 ml of 1 M aqueous potassium hexacyanoferrate (III) (potassium ferricyanide) solution are added to the electrolysis cell. The GC electrode is connected to a BAS100B/W potentiostat (BAS), the solution is stirred at 37° C., and +500 mV is applied to the silver-silver chloride reference electrode. 1 M D-glucose solutions are added to these systems to a final concentration of 5, 10, 20, 30, 40 and 50 mM, and the steady-state current value is measured for each addition. The current values are then plotted versus the known glucose concentrations (5, 10, 20, 30, 40 and 50 mM) to prepare a calibration curve. As a result, D-glucose can be quantified with an enzyme-immobilized electrode using the FAD-binding glucose dehydrogenase of the present invention.

Since the FAD-GDH of the present invention has superior substrate specificity even when compared with Mucor-derived FAD-GDH of the prior art, it can be expected to demonstrated superior effects particularly in the case of applying to a glucose sensor in the manner described above. This is because, in a glucose sensor, the enzyme reaction is presumed to be carried out under special conditions in which a larger amount of enzyme is mounted on the sensor in comparison with the case of applying to a liquid reagent kit and the like, and under such conditions, the need to reduce the effects of coexisting substances is particularly high.

The following provides a more detailed explanation of the present invention through examples thereof. However, the technical scope of the present invention is not limited in any way by these examples.

EXAMPLE 1

(Evaluation of Substrate Specificity of the Genus Mucor-derived FAD-GDH in Yeast Expression System)

(1) Preparation of Yeast Transformant Strain Sc-Mp Expressing the Genus Mucor-Derived FAD-GDH A recombinant plasmid (puc-MGD) that encodes the FAD-GDH gene of SEQ ID NO: 2 (described as MpGDH gene in Patent Document 4) was acquired in compliance with the method described in Patent Document 4. A PCR reaction was carried out in accordance with the protocol provided by using this as a template and using the synthetic nucleotides of SEQ ID NO: 3 and 4 and Prime STAR Max DNA polymerase (Takara). The PCR reaction liquid was electrophoresed in 1.0% agarose gel, and an approximately 2 kb "insert DNA fragment" was purified using Recochip (Takara).

In addition, plasmid pYES2/CT for expression in Saccharomyces cerevisiae (Invitrogen) was treated with restrictase KpnI (New England Biolabs) followed by electrophoresing the reaction liquid following restrictase treatment in 1.0% agarose gel, and purifying an approximately 6 kb "vector DNA fragment" using Recochip (Takara).

Continuing, the purified "insert DNA fragment" and "vector DNA fragment" were linked using the In-Fusion FID Cloning Kit (Clontech) in accordance with the protocol provided to produce recombinant plasmid pYE2C-Mp in order to express MpGDH under the control of GAL1 promoter. Furthermore, GAL1 promoter is a D-galactose-inducible promoter, and gene expression downstream from the promoter is induced by culturing in a medium containing D-galactose but not containing D-glucose. This pYES2C-Mp was confirmed to encode the gene sequence of SEQ ID NO: 2 with the CEQ2000 Multi-Capillary DNA Analysis System (Beckman Coulter). Subsequently, yeast transformant strain Sc-Mp that expresses the genus Mucor-derived FAD-GDH of SEQ ID NO: 1 was acquired by transforming pYE2C-Mp to strain Inv-Sc (Invitrogen) using an S. cerevisiae transformation kit (Invitrogen).

(2) Confirmation of GDH Activity in Strain Sc-Mp and Evaluation of Substrate Specificity Yeast transformant strain Sc-Mp was cultured for 24 hours at 30° C. in 5 mL of pre-culture liquid medium (0.67% (w/v) amino acid-free yeast nitrogen base (BD), 0.192% (w/v) uracil-free yeast synthetic dropout medium additive (Sigma), 2.0% (w/v) raffinose). Subsequently, 1 mL of the pre-culture liquid was added to 4 mL of final culture liquid medium (0.67% (w/v) amino acid-free yeast nitrogen base, 0.192% (w/v) uracil-free yeast synthetic dropout medium additive, 2.5% (w/v) D-galactose, 0.75% (w/v) raffinose) followed by culturing for 16 hours at 30° C.

This culture liquid was then separated into microbial cells and culture supernatant by centrifugal separation (10,000×g, 4° C., 3 minutes), and when GDH activity was measured by the previously described enzyme activity measurement method, GDH activity in the culture supernatant was 13.1 U/mL. Next, when this activity measurement method was used to measure activity in a system in which an equimolar concentration of maltose or D-xylose was used for the substrate instead of D-glucose, the activity values were 0.114 U/mL and 0.215 U/ml, respectively. Namely, the "ratio of activity to maltose to activity to D-glucose (Mal/Glc (%))" and the "ratio of activity to D-xylose to activity to D-glucose (Xyl/Glc (%))" of Mucor-derived FAD-GDH expressed in strain Sc-Mp were determined to be 0.87% and 1.64%, respectively.

The values of (Mal/Glc (%)) and (Xyl/Glc (%)) of *Mucor*-derived FAD-GDH expressed in strain Sc-Mp were nearly equal to those obtained by measuring in the same manner after purifying FAD-GDH inherently produced in source microorganisms in the form of *Mucor* species. Namely, *Mucor*-derived FAD-GDH expressed in strain Sc-Mp was confirmed to already have sufficiently superior substrate specificity for D-glucose even when compared with various known types of FAD-GDH, and this enzyme was determined to be able to be said to be a preferable starting substance in an attempt to further improve substrate specificity through modification.

EXAMPLE 2

(Prediction of Amino Acids Located Near Substrate Binding Site in *Mucor*-Derived FAD-GDH, Production of Modified *Mucor*-derived FAD-GDH by Introduction of Mutations, and Verification of Effect of Improving Substrate Specificity)

(1) Prediction of Amino Acids Located Surrounding Substrate Binding Site in *Mucor*-Derived FAD-GDH A protein having high homology with the amino acid sequence of a type of *Mucor*-derived FAD-GDH derived from *Mucor* species disclosed by the applicant in Japanese Patent No. 4648993 in the form of *Mucor*-derived FAD-GDH has not been found among various types of previously known proteins. Thus, it was not thought to be easy to predict the three-dimensional structure of *Mucor*-derived FAD-GDH or amino acids located near the active site based on the three-dimensional structure of known proteins predicted to be similar enzymes as in the case of the existence of known proteins having high homology.

As a result of expanding the range of the search to include regions having low identity by making an actual BLAST search of the Protein Data Bank (PDB), 26 amino acid sequences were found. More specifically, these included, starting with the sequence having the highest identity, 1GPE (identity: 32%, glucose oxidase), 1CF3 (identity: 31%, glucose oxidase), 1GAL (identity: 31%, glucose oxidase), 3QVP (identity: 31%, glucose oxidase), 3QVR (identity: 31%, glucose oxidase), 3FIM (identity: 26%, allyl alcohol oxidase) and 3Q9T (identity: 22%, formic acid oxidase). Among the 26 types of proteins found, five were glucose oxidases while the remainder consisted of functionally different proteins.

Among the proteins found in the BLAST search of the PDB, although that having the highest identity was glucose oxidase derived from *Penicillium amagasakiense* (*P. amagasakiense*) (PDB ID: 1 GPE), the identity thereof was low at only 32%. The amino acid sequence of the glucose oxidase of *P. amagasakiense* is shown in SEQ ID NO: 5. It would not be reasonable to consider that a person with ordinary skill in the art would predict that proteins having such a low degree of identity would have similar functions. Moreover, it would also not be reasonable to consider that a person with ordinary skill in the art would expect that an amino acid at the same position in one sequence corresponding to the position of an amino acid sequence in another sequence would be able to demonstrate the same functional effect by comparing amino acid sequences known to have such a low degree of identity. In actuality, the fact that it would be difficult to say that known proteins found to have this degree of identity are the same enzyme is as previously described.

Since it is recognized that it would not be reasonable to carry out analyses based on the three-dimensional structure of proteins having low identity as is described above, it was decided to acquire the three-dimensional structure of *P. amagasakiense*-derived glucose oxidase from a protein structure data bank (http://www.pdb.org/pdb/home/home/do), and infer those amino acids located near the substrate binding site of *Mucor*-derived FAD-GDH in the manner indicated below.

In general, the active center of an oxidation-reduction enzyme having flavin as a coenzyme is known to be located around the re-face of an isoalloxazine ring. Therefore, amino acids displaying the three-dimensional structure of glucose oxidase derived from *P. amagasakiense* with the three-dimensional structure analysis software PyMOL 0.99rc6 available from the web site, and located so as to surround the re-face of the isoalloxazine ring of FAD, were presumed to be amino acids located near the substrate binding site of glucose oxidase derived from *P. amagasakiense*. As a result, amino acid sequences having tyrosine at position 73, glycine at position 112, arginine at position 516 and histidine at position 563 in the amino acid sequence of SEQ ID NO: 5 were predicted to be candidates for amino acids having the possibility of being located near the substrate binding site in glucose oxidase derived from *P. amagasakiense*.

Next, a comparison was made between the genus *Mucor*-derived FAD-GDH of SEQ ID NO: 1 and the amino acid sequence of glucose oxidase derived from *P. amagasakiense* of SEQ ID NO: 5 using the web-based multiple alignment program, ClustalW (http://www.genome.jp/tools/clustalw/). The results of comparing these amino acid sequences are shown in FIG. 1. Based on FIG. 1, tyrosine at position 73, glycine at position 112, arginine at position 516 and histidine at position 563 of glucose oxidase derived from *P. amagasakiense* were predicted to correspond to tyrosine at position 79, glycine at position 120, arginine at position 566 and histidine at position 613 in *Mucor*-derived FAD-GDH, and these amino acids were predicted to be located near the substrate binding site in *Mucor*-derived FAD-GDH.

The inventors of the present invention proposed a basic approach for creating the FAD-GDH of the present invention based on the aforementioned analysis. However, when considering the low degree of identity between *Mucor*-derived FAD-GDH and *P. amagasakiense*-derived glucose oxidase, as well as that the substrate binding site in *P. amagasakiense*-derived glucose oxidase was merely determined on the basis of an indirect inference, it cannot be considered to be likely that the actual enzyme three-dimensional structure would be as predicted above. In addition, even in the case the amino acids at several positions in *Mucor*-derived FAD-GDH were actually the same residues at the corresponding positions, it would normally be recognized by a person with ordinary skill in the art that it would be difficult to say that this is necessarily related to the three-dimensional characteristics of *P. amagasakiense*-derived glucose oxidase or an effect thereof. Thus, since the findings of the present invention exceed that which would be reasonably recognized or predicted by a person with ordinary skill in the art, even in the case of having actually made a search based on this approach, a considerable amount of trial and error would be required in order to obtain the findings of the present invention.

(2) Introduction of Site-Specific Mutation Near Predicted Substrate Binding Site in *Mucor* Species-Derived FAD-GDH As a result of the aforementioned indirect inference, it was decided to introduce site-specific mutations consisting of substituting amino acids with various type of other amino acids at those locations predicted to have the possibility of being located near the substrate binding site in *Mucor*-derived FAD-GDH, namely tyrosine at position 79, glycine at position 120, arginine at position 566 and histidine at position 613 in SEQ ID NO: 1.

PCR reactions were carried out under the following conditions using recombinant plasmid pYE2C-Mp as template and the synthetic nucleotides of SEQ ID NO: 26 and 27 by using KOD-Plus- (Toyobo).

Namely, 5 µl of 10×KOD-Plus- buffer, 5 µl of a mixed solution of dNTPs prepared so that the concentration of each dNTP was 2 mM, 2 µl of 25 mM MgSO₄, 50 ng of pYE2C-Mp serving as template, 15 pmol of each of the aforementioned synthetic oligonucleotides and 1 unit of KOD-Plus- were added followed by bringing to a final volume of 50 µl with sterile water. The prepared reaction liquid was incubated for 2 minutes at 94° C. followed by repeating 30 cycles consisting of 15 seconds at 94° C., 30 seconds at 55° C. and 8 minutes at 68° C. using a thermal cycler (Eppendorf).

A portion of the reaction liquid was electrophoresed in 1.0% agarose gel to confirm that DNA of approximately 8 kbp is specifically amplified. The resulting DNA was treated using restrictase DpnI (New England Biolabs) followed by cleaving the remaining template DNA, linking to the vector, transforming *E. coli* strain JM109 (Nippon Gene) and applying to LB-amp agar medium. The colonies that formed were inoculated into LB-amp liquid medium followed by shake culturing and isolating the plasmid DNA using the GenElute Plasmid Miniprep Kit (Sigma) in accordance with the protocol provided. The base sequence of DNA that encoded FAD-GDH in the plasmid was determined using the CEQ2000 Multi Capillary DNA Analysis System (Beckman Coulter), and a recombinant plasmid was acquired that encoded modified *Mucor*-derived FAD-GDH in which tyrosine at position 79 was substituted for alanine in the amino acid sequence described in SEQ ID NO: 2 (pYE2C-Mp-Y79A).

PCR reactions were similarly carried out by respectively using the combinations of synthetic nucleotides having the sequence ID numbers shown in Table 1, *E. coli* strain JM109 was transformed using vectors containing amplified DNA, and the base sequences of DNA encoding *Mucor*-derived FAD-GDH in the plasmid DNA retained by the formed colonies were determined to acquire recombinant plasmids consisting of pYE2C-Mp-Y79A, pYE2C-Mp-Y79V, pYE2C-Mp-Y79P, pYE2C-Mp-Y79C, pYE2C-Mp-Y79N, pYE2C-Mp-Y79Q, pYE2C-Mp-Y79S, pYE2C-Mp-Y79T, pYE2C-Mp-Y79H, pYE2C-Mp-Y79F, pYE2C-Mp-Y79W, pYE2C-Mp-Y79K, pYE2C-Mp-G120H, pYE2C-Mp-G120C, pYE2C-Mp-G120E, pYE2C-Mp-G120K, pYE2C-Mp-G120W, pYE2C-Mp-G120M, pYE2C-Mp-R566H, pYE2C-Mp-R566M, pYE2C-Mp-R566Y, pYE2C-Mp-R566Q, pYE2C-Mp-R566E, pYE2C-Mp-R566K, pYE2C-Mp-H613K, pYE2C-Mp-H613R, pYE2C-Mp-H613N and pYE2C-Mp-H613D in which tyrosine at position 79 for alanine, tyrosine at position 79 for valine, tyrosine at position 79 for proline, tyrosine at position 79 for cysteine, tyrosine at position 79 for arginine, tyrosine at position 79 for glutamine, tyrosine at position 79 for serine, tyrosine at position 79 for threonine, tyrosine at position 79 for histidine, tyrosine at position 79 for phenylalanine, tyrosine at position 79 for tryptophan, tyrosine at position 79 for lysine, glycine at position 120 for histidine, glycine at position 120 for cysteine, glycine at position 120 for glutamic acid, glycine at position 120 for lysine, glycine at position 120 for tryptophan, glycine at position 120 for methionine, arginine at position 566 for histidine, arginine at position 566 for methionine, arginine at position 566 for tyrosine, arginine at position 566 for glutamine, arginine at position 566 for glutamic acid, arginine at position 566 for lysine, histidine at position 613 for lysine, histidine at position 613 for arginine, histidine at position 613 for asparagine and histidine at position 613 for aspartic acid were respectively substituted in the amino acid sequence described in SEQ ID NO: 2.

(3) Evaluation of Substrate Specificity of Various Modified *Mucor*-Derived FAD-GDH Introduced with Site-Specific Mutations Strain Inv-Sc was transformed and transformants were cultured in the same manner as previously described using recombinant plasmids pYE2C-Mp-Y79A, pYE2C-Mp-Y79V, pYE2C-Mp-Y79P, pYE2C-Mp-Y79C, pYE2C-Mp-Y79N, pYE2C-Mp-Y79Q, pYE2C-Mp-Y79S, pYE2C-Mp-Y79T, pYE2C-Mp-Y79H, pYE2C-Mp-Y79F, pYE2C-Mp-Y79W, pYE2C-Mp-Y79K, pYE2C-Mp-G120H, pYE2C-Mp-G120C, pYE2C-Mp-G120E, pYE2C-Mp-G120K, pYE2C-Mp-G120W, pYE2C-Mp-G120M, pYE2C-Mp-R566H, pYE2C-Mp-R566M, pYE2C-Mp-R566Y, pYE2C-Mp-R566Q, pYE2C-Mp-R566E, pYE2C-Mp-R566K, pYE2C-Mp-H613K, pYE2C-Mp-H613R, pYE2C-Mp-H613N and pYE2C-Mp-H613D encoding modified *Mucor*-derived FAD-GDH containing site-specific mutations, followed by measurement of FAD-GDH activity in the culture supernatant.

Continuing, the ratio of activity to an equimolar concentration of D-xylose to activity to D-glucose (Xyl/Glc (%)) and/or the ratio of activity to an equimolar concentration of maltose to activity to D-glucose (Mal/Glc (%)) were measured under reaction conditions based on the previously described activity measurement method using the culture supernatants of each of the aforementioned *Mucor*-derived FAD-GDH mutants for which GDH activity had been confirmed.

The values of Xyl/Glc (%) and Mal/Glc (%) along with the "Xyl/Glc ratio (%)" and "Mal/Glc ratio (%)", which represent the relative substrate specificities exhibited by modified FAD-GDH following introduction of a site-specific mutation based on a value of 100% for the values of Xyl/Glc (%) and Mal/Glc (%) in *Mucor*-modified FAD-GDH before introducing a site-specific mutation, are shown in Table 1. In modified FAD-GDH in which the "Xyl/Glc ratio (%)" or "Mal/Glc ratio (%)" exceeds 100, the reactivity to D-xylose or maltose ends up being higher than FAD-GDH before introducing a site-specific mutation, thereby demonstrating decreased substrate specificity. Conversely, in modified FAD-GDH in which the "Xyl/Glc ratio (%)" or "Mal/Glc ratio (%)" is less than 100, reactivity to D-xylose or maltose decreases in comparison with FAD-GDH before introducing a site-specific mutation, thereby demonstrating increased substrate specificity, and the degree of that increase becomes larger the smaller the value. Furthermore, those mutants for which the measured value is indicated with a "-" indicate that GDH activity decreased considerably or that GDH activity was lost. The results shown in Table 1 were all measured under the same measurement conditions.

TABLE 1

| Plasmid | Amino acid mutation | Sequence numbers of oligonucleotides used | Mal/Glc (%) | Mal/Glc ratio (%) | Xyl/Glc (%) | Xyl/Glc ratio (%) |
|---|---|---|---|---|---|---|
| pYE2C-Mp | None | None | 0.87 | 100 | 1.64 | 100 |
| pYE2C-Mp-Y79A | Y79A | 6, 7 | 0.98 | 113 | 1.37 | 84 |
| pYE2C-Mp-Y79V | Y79V | 8, 7 | — | — | — | — |
| pYE2C-Mp-Y79P | Y79P | 9, 7 | — | — | — | — |
| pYE2C-Mp-Y79C | Y79C | 10, 7 | — | — | — | — |
| pYE2C-Mp-Y79N | Y79N | 11, 7 | 0.82 | 94 | 1.17 | 71 |
| pYE2C-Mp-Y79Q | Y79Q | 12, 7 | 4.24 | 488 | 2.23 | 136 |
| pYE2C-Mp-Y79S | Y79S | 13, 7 | 0.98 | 113 | 1.38 | 84 |
| pYE2C-Mp-Y79T | Y79T | 14, 7 | — | — | — | — |
| pYE2C-Mp-Y79H | Y79H | 15, 7 | — | — | — | — |
| pYE2C-Mp-Y79F | Y79F | 16, 7 | 1.18 | 135 | 1.03 | 63 |
| pYE2C-Mp-Y79W | Y79W | 17, 7 | 2.13 | 245 | 2.79 | 170 |
| pYE2C-Mp-Y79K | Y79K | 18, 7 | — | — | — | — |
| pYE2C-Mp-G120H | G120H | 19, 20 | — | — | — | — |
| pYE2C-Mp-G120C | G120C | 21, 20 | — | — | — | — |
| pYE2C-Mp-G120E | G120E | 22, 20 | — | — | — | — |
| pYE2C-Mp-G120K | G120K | 23, 20 | — | — | — | — |
| pYE2C-Mp-G120W | G120W | 24, 20 | — | — | — | — |
| pYE2C-Mp-G120M | G120M | 25, 20 | — | — | — | — |
| pYE2C-Mp-R566H | R566H | 26, 27 | — | — | — | — |
| pYE2C-Mp-R566M | R566M | 28, 27 | — | — | — | — |
| pYE2C-Mp-R566Y | R566Y | 29, 27 | — | — | — | — |
| pYE2C-Mp-R566Q | R566Q | 30, 27 | — | — | — | — |
| pYE2C-Mp-R566E | R566E | 31, 27 | — | — | — | — |
| pYE2C-Mp-R566K | R566K | 32, 27 | — | — | — | — |
| pYE2C-Mp-H613K | H613K | 33, 34 | — | — | — | — |
| pYE2C-Mp-H613R | H613R | 35, 34 | — | — | — | — |
| pYE2C-Mp-H613N | H613N | 36, 34 | — | — | — | — |
| pYE2C-Mp-H613D | H613D | 37, 34 | — | — | — | — |

As shown in Table 1, many of the modified proteins produced did not possess adequate FAD-GDH activity. In addition, even among those proteins that demonstrated FAD-GDH activity, there were those in which reactivity to D-xylose or maltose was high resulting in poor substrate specificity. Among these proteins, the values of Xyl/Glc (%) and Xyl/Glc ratio (%) were determined to decrease by respectively substituting tyrosine at position 79 in SEQ ID NO: 1 with alanine, asparagine, serine or phenylalanine. In proteins in which tyrosine was substituted with asparagine or phenylalanine in particular, the Xyl/Glc ratio (%) decreased by 20% or more, thereby demonstrating a remarkable degree of improvement of substrate specificity. In addition, in the case of the modified protein in which tyrosine at position 79 in SEQ ID NO: 1 was substituted with asparagine, values for both Mal/Glc (%) and Mal/Glc ratio (%) also decreased slightly, and it was determined that that not only reactivity with respect to D-xylose, but also reactivity with respect to maltose, is equal to or better than that prior to introducing a site-specific mutation.

Namely, as a result of respectively mutating amino acids at a plurality of sites indirectly inferred based on the approach described in (1) above, although modified forms demonstrating desired effects were unable to be acquired easily, during the course of searching, modified forms were able to be acquired that demonstrated preferable effects in the case of mutating the amino acid at the location of position 79 and substituting for a certain type of amino acid residue.

EXAMPLE 3

(Production of Modified *Mucor*-derived FAD-GDH Introduced with Site-specific Mutation Near Indirectly Predicted Substrate Binding Site)

(1) Introduction of Site-Specific Mutation Near Predicted Substrate Binding Site As indicated in Example 2, since modified forms having desired properties were able to be acquired for a portion of the modified forms produced, site-specific mutations were also attempted to be introduced for those amino acids in proximity to each of tyrosine at position 79, glycine at position 120, arginine at position 566 and histidine at position 613 that were mutated in Example 2.

More specifically, recombinant plasmids encoding modified FAD-GDH introduced with a target site-specific mutation were prepared by using recombinant plasmid pYE2C-Mp as template in compliance with Example 2 by using various combinations of synthetic nucleotides as primers. Typical examples of the modified forms produced are shown in Table 2. More specifically, these modified forms consisted of mutants obtained by substituting glycine at position 77 for alanine, methionine at position 78 for cysteine, methionine at position 78 for aspartic acid, methionine at position 78 for asparagine, methionine at position 78 for glutamic acid, methionine at position 78 for glutamine, glutamine at position 81 for leucine, glutamine at position 81 for phenylalanine, glutamine at position 81 for asparagine, leucine at position 121 for cysteine, leucine at position 121 for methionine, valine at position 122 for threonine, valine at position 122 for isoleucine, valine at position 122 for alanine, valine at position 122 for methionine, valine at position 122 for cysteine, tryptophan at position 123 for cysteine, tryptophan at position 123 for phenylalanine, tryptophan at position 123 for histidine, tryptophan at position 123 for valine, tryptophan at position 123 for serine, aspartic acid at position 568 for asparagine, aspartic acid at position 568 for glutamic acid, tryptophan at position 569 for phenylalanine, tryptophan at position 569 for tyrosine, serine at position 612 for alanine, serine at position 612 for cysteine and serine at position 612 for threonine in SEQ ID NO: 1, and recombinant plasmids containing genes encoding these mutants were designated as pYE2C-Mp-G77A, pYE2C-Mp-M78C, pYE2C-Mp-M78D, pYE2C-Mp-M78N, pYE2C-Mp-M78E, pYE2C-Mp-M78Q, pYE2C-Mp-Q81L, pYE2C-Mp-Q81F, pYE2C-Mp-Q81N, pYE2C-Mp-L121C, pYE2C-Mp-L121M, pYE2C-Mp-V122T, pYE2C-Mp-V121I, pYE2C-Mp-V122A, pYE2C-Mp-V122M, pYE2C-Mp-V122C, pYE2C-Mp-W123C, pYE2C-Mp-W123F, pYE2C-Mp-W123H, pYE2C-Mp-W123V, pYE2C-Mp-W123 S, pYE2C-Mp-D568N, pYE2C-Mp-D568E, pYE2C-Mp-W569F, pYE2C-Mp-W569Y, pYE2C-Mp-S612A, pYE2C-Mp-S612C and pYE2C-Mp-S612T.

(2) Evaluation of Substrate Specificity of Various Types of Modified *Mucor*-Derived FAD-GDH Introduced with Site-Specific Mutations Strain Inv-Sc was transformed in the same manner as Example 2 using the aforementioned recombinant plasmids pYE2C-Mp-G77A, pYE2C-Mp-M78C, pYE2C-Mp-M78D, pYE2C-Mp-M78N, pYE2C-Mp-M78E, pYE2C-Mp-M78Q, pYE2C-Mp-Q81L, pYE2C-Mp-Q81F, pYE2C-Mp-Q81N, pYE2C-Mp-L121C, pYE2C-Mp-L121M, pYE2C-Mp-V122T, pYE2C-Mp-V121I, pYE2C-Mp-V122A, pYE2C-Mp-V122M, pYE2C-Mp-V122C, pYE2C-Mp-W123C, pYE2C-Mp-W123F, pYE2C-Mp-W123H, pYE2C-Mp-W123V, pYE2C-Mp-W123S, pYE2C-Mp-D568N, pYE2C-Mp-D568E, pYE2C-Mp-W569F, pYE2C-Mp-W569Y, pYE2C-Mp-S612A, pYE2C-Mp-S612C and pYE2C-Mp-S612T encoding modified *Mucor*-derived FAD-GDH introduced with site-specific mutations, followed by culturing each of the transformants and confirming GDH activity in the culture supernatants.

Continuing, Mal/Glc (%), Mal/Glc ratio (%), Xyl/Glc (%) and Xyl/Glc ratio (%) were measured in the same manner as Example 2. The results are shown in Table 2.

TABLE 2

| Plasmid | Amino acid mutation | Sequence numbers of oligonucleotides used | Mal/Glc (%) | Mal/Glc ratio (%) | Xyl/Glc (%) | Xyl/Glc ratio (%) |
| --- | --- | --- | --- | --- | --- | --- |
| pYE2C-Mp | None | None | 0.87 | 100 | 1.64 | 100 |
| pYE2C-Mp-G77A | G77A | 38, 39 | 1.08 | 125 | 1.93 | 118 |
| pYE2C-Mp-M78C | M78C | 40, 41 | 0.92 | 106 | 0.77 | 47 |
| pYE2C-Mp-M78D | M78D | 42, 41 | 2.67 | 307 | 1.33 | 81 |
| pYE2C-Mp-M78N | M78N | 43, 41 | 1.06 | 122 | 0.71 | 43 |
| pYE2C-Mp-M78E | M78E | 44, 41 | 0.65 | 75 | 1.10 | 67 |
| pYE2C-Mp-M78Q | M78Q | 45, 41 | 0.45 | 52 | 0.90 | 55 |
| pYE2C-Mp-Q81L | Q81L | 46, 47 | 0.52 | 60 | 1.55 | 95 |
| pYE2C-Mp-Q81F | Q81F | 48, 47 | 0.54 | 62 | 1.99 | 121 |
| pYE2C-Mp-Q81N | Q81N | 49, 47 | 0.45 | 51 | 1.27 | 78 |
| pYE2C-Mp-L121C | L121C | 50, 51 | 1.35 | 156 | 1.18 | 72 |
| pYE2C-Mp-L121M | L121M | 52, 51 | 0.54 | 63 | 0.88 | 54 |
| pYE2C-Mp-V122T | V122T | 53, 54 | 0.24 | 27 | 1.94 | 118 |
| pYE2C-Mp-V122I | V122I | 55, 54 | 0.71 | 81 | 9.53 | 582 |
| pYE2C-Mp-V122A | V122A | 56, 54 | 0.42 | 48 | 2.08 | 127 |
| pYE2C-Mp-V122M | V122M | 57, 54 | 1.30 | 150 | 4.94 | 301 |
| pYE2C-Mp-V122C | V122C | 58, 54 | 0.46 | 53 | 1.64 | 100 |
| pYE2C-Mp-W123C | W123C | 59, 60 | 0.37 | 42 | 0.37 | 22 |
| pYE2C-Mp-W123F | W123F | 61, 60 | 0.39 | 45 | 0.65 | 40 |
| pYE2C-Mp-W123H | W123H | 62, 60 | 0.16 | 19 | 0.49 | 30 |
| pYE2C-Mp-W123V | W123V | 63, 60 | 0.42 | 48 | 0.77 | 47 |
| pYE2C-Mp-W123S | W123S | 64, 60 | 0.32 | 37 | 0.32 | 20 |
| pYE2C-Mp-D568N | D568N | 65, 66 | — | — | — | — |
| pYE2C-Mp-D568E | D568E | 67, 66 | — | — | — | — |
| pYE2C-Mp-W569F | W569F | 68, 69 | 0.28 | 32 | 0.55 | 34 |
| pYE2C-Mp-W569Y | W569Y | 70, 69 | 0.21 | 24 | 0.55 | 34 |
| pYE2C-Mp-S612A | S612A | 71, 72 | 1.06 | 122 | 1.80 | 110 |
| pYE2C-Mp-S612C | S612C | 73, 72 | 0.58 | 67 | 1.05 | 64 |
| pYE2C-Mp-S612T | S612T | 74, 72 | 0.56 | 64 | 1.20 | 73 |

On the basis of Table 2, Mal/Glc (%) and Mal/Glc ratio (%) were determined to decrease as a result of substituting methionine at position 78 for glutamic acid, methionine at position 78 for glutamine, glutamine at position 81 for leucine, glutamine at position 81 for phenylalanine, glutamine at position 81 for asparagine, leucine at position 121 for methionine, valine at position 122 for threonine, valine at position 122 for isoleucine, valine at position 122 for alanine, valine at position 122 for cysteine, tryptophan at position 123 for cysteine, tryptophan at position 123 for phenylalanine, tryptophan at position 123 histidine, tryptophan at position 123 for valine, tryptophan at position 123 for serine, tryptophan at position 569 for phenylalanine, tryptophan at position 569 for tyrosine, serine at position 612 for cysteine or serine at position 612 for threonine in SEQ ID NO: 1.

Particularly in the case of substituting methionine at position 78 for glutamic acid, methionine at position 78 for glutamine, glutamine at position 81 for leucine, glutamine at position 81 for phenylalanine, glutamine at position 81 for asparagine, leucine at position 121 for methionine, valine at position 122 for threonine, valine at position 122 for alanine, valine at position 122 for cysteine, tryptophan at position 123 for cysteine, tryptophan at position 123 for phenylalanine, tryptophan at position 123 for histidine, tryptophan at position 123 for valine, tryptophan at position 123 for serine, tryptophan at position 569 for phenylalanine, tryptophan at position 569 for tyrosine, serine at position 612 for cysteine or serine at position 612 for threonine in SEQ ID NO: 1, Mal/Glc ratio (%) decreased by 20% or more, and the degree of improvement of substrate specificity was remarkable.

In addition, Xyl/Glc (%) and Xyl/Glc ratio (%) were determined to decrease as a result of substituting methionine at position 78 for cysteine, methionine at position 78 for aspartic acid, methionine at position 78 for asparagine, methionine at position 78 for glutamic acid, methionine at position 78 for glutamine, glutamine at position 81 for leucine, glutamine at position 81 for asparagine, leucine at position 121 for cysteine, leucine at position 121 for methionine, tryptophan at position 123 for cysteine, tryptophan at position 123 for phenylalanine, tryptophan at position 123 for histidine, tryptophan at position 123 for valine, tryptophan at position 123 for serine, tryptophan at position 569 for phenylalanine, tryptophan at position 569 for tyrosine, serine at position 612 for cysteine or serine at position 612 for threonine in SEQ ID NO: 1.

Particularly in the case of substituting methionine at position 78 for cysteine, methionine at position 78 for asparagine, methionine at position 78 for glutamic acid, methionine at position 78 for glutamine, glutamine at position 81 for asparagine, leucine at position 121 for cysteine, leucine at position 121 for methionine, tryptophan at position 123 for cysteine, tryptophan at position 123 for phenylalanine, tryptophan at position 123 for histidine, tryptophan at position 123 for valine, tryptophan at position 123 for serine, tryptophan at position 569 for phenylalanine, tryptophan at position 569 for tyrosine, serine at position 612 for cysteine or serine at position 612 for threonine in SEQ ID NO: 1, Xyl/Glc ratio (%) decreased by 20% or more, and the degree of improvement of substrate specificity was remarkable.

Moreover, in modified FAD-GDH in which methionine at position 78 for glutamic acid, methionine at position 78 for glutamine, glutamine at position 81 for asparagine, leucine at position 121 for methionine, tryptophan at position 123 for cysteine, tryptophan at position 123 for phenylalanine, tryptophan at position 123 for histidine, tryptophan at position 123 for valine, tryptophan at position 123 for serine, tryptophan at position 569 for phenylalanine, tryptophan at position 569 for tyrosine, serine at position 612 for cysteine or serine at position 612 for threonine was substituted, both Mal/Glc ratio (%) and Xyl/Glc ratio (%) decreased by 20% or more, decreased by 40% or more or 50% or more in more remarkable cases, and decreased by 60% or more in extremely remarkable cases, and were determined to have extremely high substrate specificity.

EXAMPLE 4

(Evaluation of Substrate Specificity of Multiple Mutants of Modified *Mucor*-derived FAD-GDH)
(1) Introduction of Multiple Substrate Specificity-Improving Mutations in *Mucor*-Derived FAD-GDH A variety of mutants were acquired into which were introduced multiple target site-specific mutations by using recombinant plasmid pYE2C-Mp-W569Y as template and combining various types of synthetic nucleotides in compliance with the methods of Example 2 and Example 3 based on the findings obtained in Example 2 and Example 3. Typical examples of the modified forms produced are shown in Table 3. More specifically, these modified forms consisted of mutants obtained by substituting tryptophan at position 569 for tyrosine in SEQ ID NO: 1, and further substituting methionine at position 78 for cysteine, methionine at position 78 for asparagine, methionine at position 78 for glutamic acid, methionine at position 78 for glutamine, tyrosine at position 79 for phenylalanine, tyrosine at position 79 for asparagine, glutamine at position 81 for asparagine, leucine at position 121 for methionine, valine at position 122 for cysteine, tryptophan at position 123 for phenylalanine, tryptophan at position 123 for valine, serine at position 612 for cysteine and serine at position 612 for threonine in SEQ ID NO: 1, and recombinant plasmids containing genes encoding these mutants were designated as pYE2C-MpY-M78C, pYE2C-MpY-M78N, pYE2C-MpY-M78E, pYE2C-MpY-M78Q, pYE2C-MpY-Y79F, pYE2C-MpY-Y79N, pYE2C-MpY-Q81N, pYE2C-MpY-L121M, pYE2C-MpY-V122C, pYE2C-MpY-W123F, pYE2C-MpY-W123V, pYE2C-MpY-S612C and pYE2C-MpY-S612T.

In addition, mutants were acquired into which were introduced multiple target site-specific mutations by using recombinant plasmid pYE2C-MpY-S612C as template and combining the synthetic nucleotides shown in Table 3 in the same manner as previously described. Typical examples of the modified forms produced are shown in Table 3. These modified forms consisted of mutants obtained by substituting tryptophan at position 569 for tyrosine in SEQ ID NO: 1, and further substituting serine at position 612 for cysteine and substituting methionine at position 78 for asparagine in SEQ ID NO: 1, and the recombinant plasmid containing a gene encoding these mutants was designated as pYE2C-MpYC-M78N.

Moreover, mutants were acquired into which were introduced multiple target site-specific mutations by using recombinant plasmid pYE2C-Mp-W123F as template and combining the synthetic nucleotides shown in Table 3 in the same manner as previously described. Typical examples of the modified forms produced are shown in Table 3. More specifically, these modified forms consisted of mutants obtained by substituting tryptophan at position 123 for phenylalanine in SEQ ID NO: 1, and further substituting leucine at position 121 for methionine and substituting serine at position 612 for threonine, and recombinant plasmids containing genes encoding each of these mutants were designated as pYE2C-MpF-L121M and pYE2C-MpF-S612T.

Moreover, mutants were acquired into which were introduced multiple target site-specific mutations by using recombinant plasmid pYE2C-Mp-W123V as template and combining the synthetic nucleotides shown in Table 3 in the same manner as previously described. Typical examples of the modified forms produced are shown in Table 3. More specifically, these modified forms consisted of mutants obtained by substituting tryptophan at position 123 for valine in SEQ ID NO: 1, and further substituting leucine at position 121 for methionine and substituting serine at position 612 for threonine, and recombinant plasmids containing genes encoding each of these mutants were designated as pYE2C-MpV-L121M and pYE2C-MpV-S612T.

(2) Evaluation of Substrate Specificity of Various Types of Modified *Mucor*-Derived FAD-GDH Introduced with Multiple Site-Specific Mutations Strain Inv-Sc was transformed in the same manner as previously described using recombinant plasmids pYE2C-MpY-M78C, pYE2C-MpY-M78N, pYE2C-MpY-M78E, pYE2C-MpY-M78Q, pYE2C-MpY-Y79F, pYE2C-MpY- Y79N, pYE2C-MpY-Q81N, pYE2C-MpY-L121M, pYE2C-MpY-V122C, pYE2C-MpY-W123F, pYE2C-MpY-W123V, pYE2C-MpY-S612C, pYE2C-MpY-S612T, pYE2C-MpYC-M78N, pYE2C-MpF-L121M, pYE2C-MpF-S612T, pYE2C-MpV-L121M and pYE2C-MpV-5612T encoding modified *Mucor*-derived FAD-GDH introduced with multiple site-specific mutations, followed by culturing each of the transformants and confirming GDH activity in the culture supernatants.

Continuing, (Mal/Glc) (%), Mal/Glc) ratio (%), (Xyl/Glc) (%) and (Xyl/Glc) ratio (%) were measured in the same manner as Example 2. The results are shown in Table 3.

In addition, as shown in Table 3, Mal/Glc (%), Mal/Glc ratio (%), Xyl/Glc (%) and Xyl/Glc ratio (%) were each determined to decrease more in a triple mutant obtained by substituting tryptophan at position 569 for tyrosine, substituting serine at position 612 for cysteine and further substituting methionine at position 79 for asparagine in SEQ ID NO: 1 in comparison with a double mutant obtained by substituting tryptophan at position 569 for tyrosine and substituting serine at position 612 for cysteine in SEQ ID NO: 1. This multiple mutant can be said to demonstrate even more superior substrate specificity in addition to the effects of each mutation site.

TABLE 3

| Plasmid | Amino acid mutation | Sequence numbers of oligonucleotides used | Mal/Glc (%) | Mal/Glc ratio (%) | Xyl/Glc (%) | Xyl/Glc ratio (%) |
|---|---|---|---|---|---|---|
| pYE2C-Mp | None | None | 0.756 | 100.0 | 1.43 | 100.0 |
| pYE2C-Mp-W569Y | W569Y | 68, 69 | 0.198 | 26.2 | 0.512 | 35.9 |
| pYE2C-MpY-M78C | W569Y/M78C | 40, 41 | 0.223 | 29.5 | 0.535 | 37.4 |
| pYE2C-MpY-M78N | W569Y/M78N | 43, 41 | 0.199 | 26.3 | 0.409 | 28.7 |
| pYE2C-MpY-M78E | W569Y/M78E | 44, 41 | 0.185 | 24.5 | 0.437 | 30.6 |
| pYE2C-MpY-M78Q | W569Y/M78Q | 45, 41 | 0.202 | 26.8 | 0.564 | 39.5 |
| pYE2C-MpY-Y79F | W569Y/Y79F | 16, 7 | 0.273 | 36.1 | 0.512 | 35.9 |
| pYE2C-MpY-Y79N | W569Y/Y79N | 11, 7 | 0.274 | 36.3 | 0.993 | 69.5 |
| pYE2C-MpY-Q81N | W569Y/Q81N | 49, 47 | 0.240 | 31.7 | 0.608 | 42.6 |
| pYE2C-MpY-L121M | W569Y/L121M | 52, 51 | 0.175 | 23.1 | 0.498 | 34.9 |
| pYE2C-MpY-V122C | W569Y/V122C | 58, 54 | 0.158 | 20.9 | 0.901 | 63.1 |
| pYE2C-MpY-W123F | W569Y/W123F | 61, 60 | 0.205 | 27.1 | 0.482 | 33.8 |
| pYE2C-MpY-W123V | W569Y/W123V | 63, 60 | 0.160 | 21.1 | 0.405 | 28.4 |
| pYE2C-MpY-S612C | W569Y/S612C | 73, 72 | 0.181 | 24.0 | 0.394 | 27.6 |
| pYE2C-MpY-S612T | W569Y/S612T | 74, 72 | 0.215 | 28.5 | 0.498 | 34.9 |
| pYE2C-MpYC-M78N | W569Y/S612C/M78N | 43, 41 | 0.070 | 9.3 | 0.327 | 22.9 |
| pYE2C-Mp-W123F | W123F | 61, 60 | 0.385 | 50.9 | 0.735 | 51.4 |
| pYE2C-MpF-L121M | W123F/L121M | 75, 60 | 0.375 | 49.6 | 0.550 | 38.5 |
| pYE2C-MpF-S612T | W123F/S612T | 74, 72 | 0.434 | 57.4 | 0.542 | 37.9 |
| pYE2C-Mp-W123V | W123V | 63, 60 | 0.424 | 56.1 | 0.696 | 48.7 |
| pYE2C-MpV-L121M | W123V/L121M | 76, 60 | 0.399 | 52.8 | 0.555 | 38.8 |
| pYE2C-MpV-S612T | W123V/S612T | 74, 72 | 0.465 | 61.5 | 0.775 | 54.3 |

On the basis of Table 3, Mal/We (%) and Mal/Glc ratio (%) were determined to decrease more in a double mutant obtained by substituting tryptophan at position 569 for tyrosine and further substituting valine at position 122 for cysteine in SEQ ID NO: 1 in comparison with a single mutant obtained by substituting tryptophan at position 569 for tyrosine in SEQ ID NO: 1.

In addition, Xyl/Glc (%) and Xyl/Glc ratio (%) were determined to decrease more in a double mutant obtained by substituting tryptophan at position 569 for tyrosine and further substituting methionine at position 78 for asparagine, tryptophan at position 123 for phenylalanine or serine at position 612 for threonine in SEQ ID NO: 1 in comparison with a single mutant obtained by substituting tryptophan at position 569 for tyrosine in SEQ ID NO: 1.

Moreover, Mal/Glc (%), Mal/Glc ratio (%), Xyl/Glc (%) and Xyl/Glc ratio (%) were each determined to decrease more in a double mutant obtained by substituting tryptophan at position 569 for tyrosine and further substituting methionine at position 78 for glutamic acid, leucine at position 121 for methionine, tryptophan at position 123 for valine or serine at position 612 for cysteine in SEQ ID NO: 1 in comparison with a single mutant obtained by substituting tryptophan at position 569 for tyrosine in SEQ ID NO: 1. Namely, several of the double mutants produced were determined to further improve substrate specificity in comparison with single mutants.

In addition, as shown in Table 3, Xyl/Glc (%) and Xyl/Glc ratio (%) were determined to decrease more in a double mutant obtained by substituting tryptophan at position 123 for phenylalanine and further substituting serine at position 612 for threonine in SEQ ID NO: 1 in comparison with a single mutant obtained by substituting tryptophan at position 123 for phenylalanine.

In addition, Mal/Glc (%), Mal/Glc ratio (%), Xyl/Glc (%) and Xyl/Glc ratio (%) were each determined to decrease more in a double mutant obtained by substituting tryptophan at position 123 for phenylalanine and further substituting leucine at position 121 for methionine in SEQ ID NO: 1 in comparison with a single mutant obtained by substituting tryptophan at position 123 for phenylalanine. This multiple mutant can be said to demonstrate even more superior substrate specificity in addition to the effects of each mutation site.

Moreover, as shown in Table 3, Mal/Glc (%), Mal/Glc ratio (%), Xyl/Glc (%) and Xyl/Glc ratio (%) were each determined to decrease more in a double mutant obtained by substituting tryptophan at position 123 for valine and further substituting leucine at position 121 for methionine in SEQ ID NO: 1 in comparison with a single mutant obtained by substituting tryptophan at position 123 for valine in SEQ ID NO: 1. This multiple mutant can be said to demonstrate even more superior substrate specificity in addition to the effects of each mutation site.

EXAMPLE 5

(Evaluation of Substrate Specificity of Various *Mucor*-derived Modified FAD-GDH by Measuring with an Enzyme Electrode)

(1) Concentration of Crude Enzyme Liquids of Various Modified *Mucor*-Derived FAD-GDH Strain Inv-Sc was transformed using each of the previously acquired recombinant plasmids pYE2C-Mp-W569Y, pYE2C-MpY-V122C, pYE2C-MpY-W123V, pYE2C-MpY-S612C and pYE2C-MpYC-M78N, and each transformant was cultured for 24 hours at 30° C. in 100 mL of pre-culture liquid medium (0.67% (w/v) amino acid-free yeast nitrogen base (BD), 0.192% (w/v) uracil-free yeast synthetic dropout medium additive (Sigma), 2.0% (w/v) raffinose). Subsequently, the entire amount of the pre-culture liquid medium was added to 1 L of final culture liquid medium (0.67% (w/v) amino acid-free yeast nitrogen base, 0.192% (w/v) uracil-free yeast synthetic dropout medium additive, 2.5% (w/v) D-galactose, 0.75% (w/v) raffinose) followed by culturing for 16 hours at 30° C.

The culture liquid was separated into microbial cells and supernatant by centrifugal separation (12,000×g, 4° C., 30 minutes) followed by recovery of the culture supernatant. Subsequently, the recovered culture supernatant was subjected to ultrafiltration treatment using an AIP-1013 ultrafiltration membrane (Asahi Chemicals), followed by concentrating using the AMICON Ultra-15 10K (Millipore) until the activity of the enzyme liquid reached 1000 U/mL or more.

(2) Evaluation of Substrate Specificity of Various Modified *Mucor*-Derived FAD-GDH by Measuring with an Enzyme Electrode)

Figure 3:
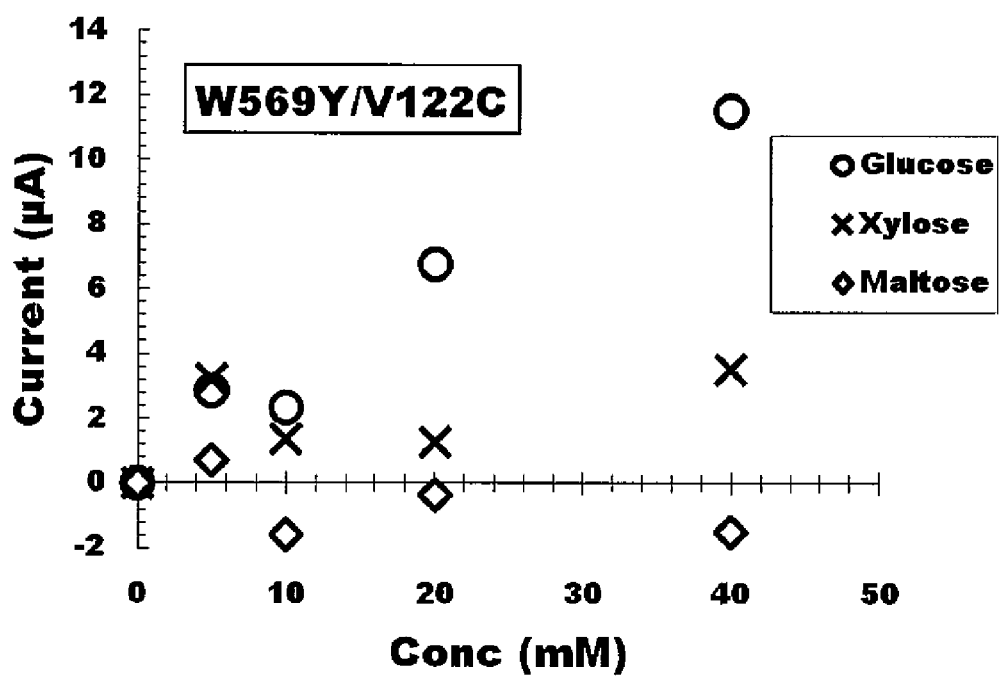
FIG. 3 is a graph showing a plot of current response values versus substrate concentration measured by enzyme electrode assay using modified Mucor-derived GDH (W569Y/N122C).
Figure 4:
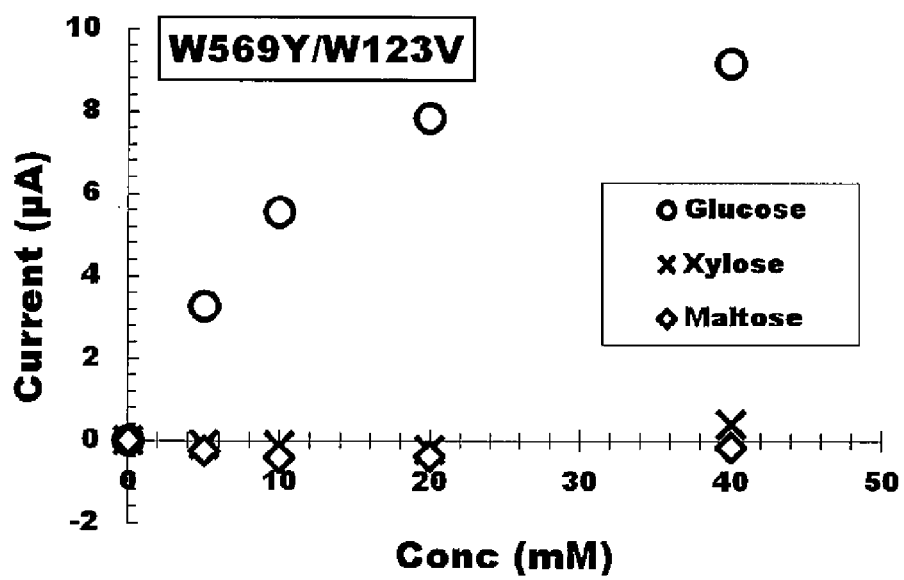
FIG. 4 is a graph showing a plot of current response values versus substrate concentration measured by enzyme electrode assay using modified Mucor-derived GDH (W569Y/W123V).
Figure 5:
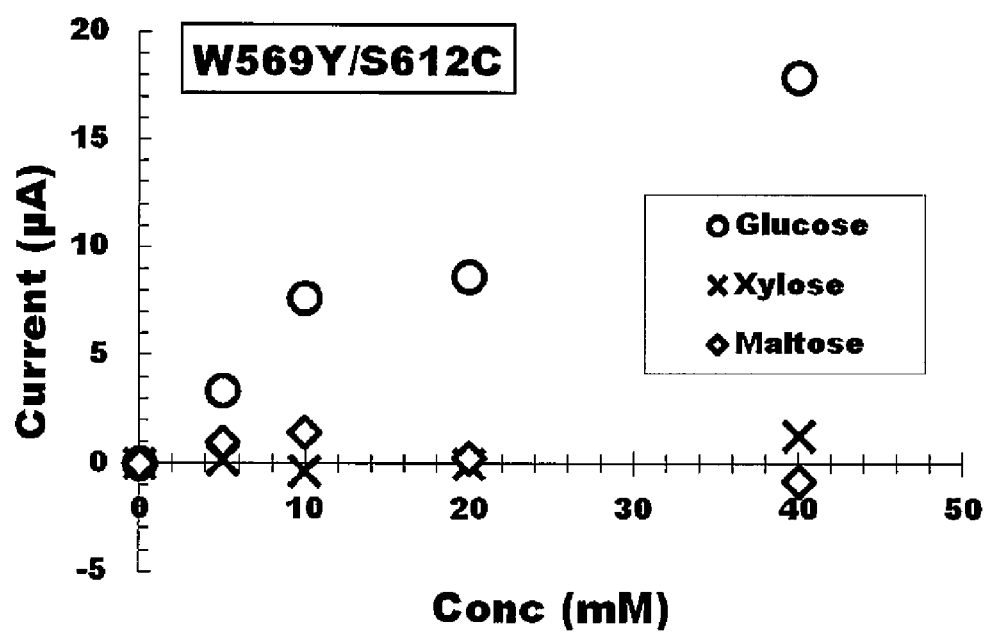
FIG. 5 is a graph showing a plot of current response values versus substrate concentration measured by enzyme electrode assay using modified Mucor-derived GDH (W569Y/S612C).
Figure 6:
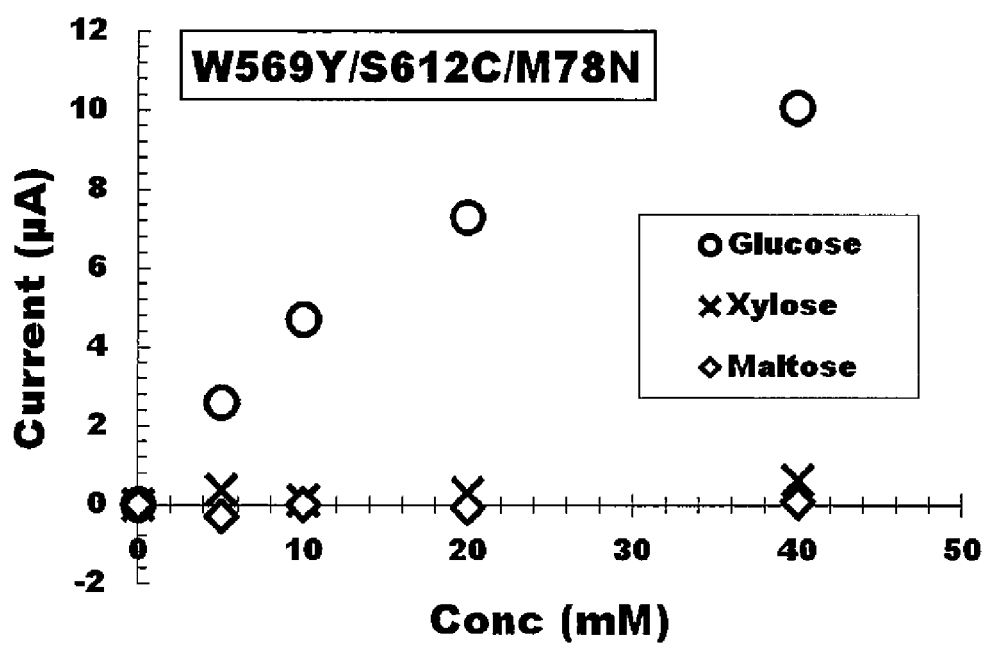
FIG. 6 is a graph showing a plot of current response values versus substrate concentration measured by enzyme electrode assay using modified Mucor-derived GDH (W569Y/S612C/M78N).

Substrate specificity of the concentrated crude enzyme liquids of various modified *Mucor*-derived FAD-GDH acquired as described above was evaluated by measuring with an enzyme electrode. More specifically, 2 µL of a solution obtained by dissolving potassium ferricyanate having a final concentration of 364 mM, phosphate buffer (pH 6.0) having a final concentration of about 100 mM and a concentrate of each enzyme having a concentration of 1000 U/mL were placed on a DEP Chip electrode (round, equipped with carbon dam ring, Bio Device Technology) printed with a carbon working electrode and silver/silver chloride reference electrode, followed by allowing to stand undisturbed for 20 minutes at 35° C. to immobilize the enzyme on the electrode (2 U/strip). Subsequently, the DEP Chip was connected to an HSV-100 Automatic Polarization System (Hokuto Denko) using a special-purpose connector. 20 µL of D-glucose, maltose and D-xylose solutions having a prescribed concentration were respectively placed on the electrode and allowed to react by applying a voltage of 300 mV followed by measurement of the current value 20 seconds later. The results of plotting the current response values versus each of reacted substrate concentrations are shown in FIGS. 2 to 6. In addition, the reactivity to maltose based on a value of 100% for reactivity to D-glucose (Mal/Glc (%)) as well as reactivity to D-xylose based on a value of 100% for reactivity to D-glucose (Xyl/Glc (%)) at respective substrate concentrations of 20 mM are shown in Table 4.

TABLE 4

| Plasmid | Amino acid mutation | Glc (%) | Mal/Glc (%) | Xyl/Glc (%) |
|---|---|---|---|---|
| pYE2C-Mp-W569Y | W569Y | 100 | 0 | 4 |
| pYE2C-MpY-V122C | W569Y/V122C | 100 | −5 | 19 |
| pYE2C-MpY-W123V | W569Y/W123V | 100 | −5 | −3 |
| pYE2C-MpY-S612C | W569Y/S612C | 100 | 3 | 0 |
| pYE2C-MpYC-M78N | W569Y/S612C/M78N | 100 | −1 | 4 |

On the basis of FIGS. 2 to 6, D-glucose concentrations and current response values demonstrated a favorable correlation in each of the genus *Mucor*-derived modified FAD-GDHs, and on the basis thereof, each *Mucor*-derived modified FAD-GDH was determined to have superior glucose quantifiability.

However, in contrast to the value of Xyl/Glc (%) of the modified FAD-GDH having only the single mutation W569Y being 4%, the modified FAD-GDH having the mutation W569Y/V122C demonstrated an Xyl/Glc (%) value of 19%, and was determined to have remarkable reactivity to D-xylose although demonstrating hardly any reactivity to maltose.

On the other hand, as shown in Table 4, the genus *Mucor*-derived modified FAD-GDHs having the mutations of W569Y, W569Y/W123V, W569Y/S612C and W569Y/S612C/M78N were determined to demonstrate hardly any reactivity to maltose and D-xylose even when evaluated by measuring with an enzyme electrode.

Furthermore, in the measurement system based on absorbance of Example 4, while the value of Xyl/Glc (%) of the modified FAD-GDH having only the mutation W569Y was 0.512%, the value of Xyl/Glc (%) in the modified FAD-GDH having the mutation W569Y/V122C was 0.901%. Namely, even if the difference in Xyl/Glc (%) in a measurement system based on absorbance in Examples 1 to 4 is only about 0.5%, in the case of comparing with a measurement system based on an enzyme electrode measurement system, the difference in the substrate specificity thereof was determined to appear more remarkably. On the basis of this finding as well, the various mutants having improved substrate specificity discovered in the present invention are required to have lower values for Xyl/Glc (%) and/or Mal/Glc (%) in particular, and this is strongly suggested to be extremely useful in applications in glucose sensors and the like in which the effect thereof is presumed to be considerable.

EXAMPLE 6

(Prediction of Amino Acids Located Near Substrate Binding Site in *Mucor*-derived FAD-GDH, Production of Modified *Mucor*-derived FAD-GDH by Introduction of Mutations, and Verification of Effect of Improving Substrate Specificity—Part 2)

The three-dimensional structure of glucose oxidase derived from *P. amagasakiense* was displayed in accordance with Example 2, and aspartic acid at position 428 was predicted to be a candidate for an amino acid located so as to surround the re-face of the isoalloxazine ring of FAD. According to FIG. 1, aspartic acid at position 428 of glucose oxidase derived from *P. amagasakiense* was predicted to be equivalent to aspartic acid at position 471 of SEQ ID NO: 1, and this amino acid was predicted to be located near the substrate-binding site in *Mucor*-derived FAD-GDH. Therefore, it was decided to introduce site-specific mutations for aspartic acid at position 471 in SEQ ID NO: 1 and its surrounding amino acids that substitute these amino acids with various types of amino acids.

More specifically, recombinant plasmids encoding modified FAD-GDH introduced with target site-specific mutations were produced using recombinant plasmid pYE2C-Mp as template in compliance with Example 2 by using combinations of each of the synthetic nucleotides shown in Table 5 as primers. Typical examples of the produced modified forms are shown in Table 5. More specifically, these modified forms consisted of mutants obtained by substituting glutamic acid at position 465 for aspartic acid, glutamic acid at position 465 for glycine, glutamic acid at position 465 for isoleucine, glutamic acid at position 465 for arginine, glutamic acid at position 465 for leucine, glutamic acid at position 465 for serine, glutamic acid at position 465 for threonine, glutamic acid at position 465 for valine, glutamic acid at position 465 for tryptophan, asparagine at position 469 for aspartic acid, asparagine at position 469 for glutamine, asparagine at position 469 for glutamic acid, aspartic acid at position 471 for asparagine, aspartic acid at position 471 for glutamic acid, aspartic acid at position 471 for glutamine, glutamine at position 473 for glutamic acid, glutamine at position 473 for asparagine, glutamine at position 473 for aspartic acid, asparagine at position 474 for aspartic acid, asparagine at position 474 for glutamine, asparagine at position 474 for glutamic acid, asparagine at position 475 for aspartic acid, asparagine at position 475 for glutamine and asparagine at position 475 for glutamic acid in SEQ ID NO: 1, and recombinant plasmids containing genes encoding each of these mutants were designated pYE2C-Mp-E465D, pYE2C-Mp-E465G, pYE2C-Mp-E465I, pYE2C-Mp-E465R, pYE2C-Mp-E465L, pYE2C-Mp-E465S, pYE2C-Mp-E465T, pYE2C-Mp-E465V, pYE2C-Mp-E46W, pYE2C-Mp-N469D, pYE2C-Mp-N469Q, pYE2C-Mp-N469E, pYE2C-Mp-D471N, pYE2C-Mp-D471E, pYE2C-Mp-D471Q, pYE2C-Mp-Q473E, pYE2C-Mp-Q473N, pYE2C-Mp-Q473D, pYE2C-Mp-N474D, pYE2C-Mp-N474Q, pYE2C-Mp-N474E, pYE2C-Mp-N475D, pYE2C-Mp-N475Q and pYE2C-Mp-N475E.

Strain Inv-Sc was transformed in the same manner as Example 2 using the aforementioned recombinant plasmids encoding modified *Mucor*-derived FAD-GDH introduced with site-specific mutations consisting of pYE2C-Mp-E465D, pYE2C-Mp-E465G, pYE2C-Mp-E465I, pYE2C-Mp-E465R, pYE2C-Mp-E465L, pYE2C-Mp-E465S, pYE2C-Mp-E465T, pYE2C-Mp-E465V, pYE2C-Mp-E46W, pYE2C-Mp-N469D, pYE2C-Mp-N469Q, pYE2C-Mp-N469E, pYE2C-Mp-D471N, pYE2C-Mp-D471E, pYE2C-Mp-D471Q, pYE2C-Mp-Q473E, pYE2C-Mp-Q473N, pYE2C-Mp-Q473D, pYE2C-Mp-N474D, pYE2C-Mp-N474Q, pYE2C-Mp-N474E, pYE2C-Mp-N475D, pYE2C-Mp-N475Q and pYE2C-Mp-N475E, followed by culturing each transformant and confirming GDH activity in the culture supernatant.

Continuing, (Xyl/Glc) ratio (%) was measured in the same manner as Example 2. The results are shown in Table 5. Furthermore, those mutants for which the measured value is indicated with a "-" indicate that GDH activity decreased considerably or that GDH activity was lost.

TABLE 5

| Plasmid | Amino acid mutation | Sequence numbers of oligonucleotides used | Xyl/Glc ratio (%) |
|---|---|---|---|
| pYE2C-Mp | None | None | 100 |
| pYE2C-Mp-E465D | E465D | 77, 78 | 64 |
| pYE2C-Mp-E465G | E465G | 79, 78 | 101 |
| pYE2C-Mp-E465I | E465I | 80, 78 | 88 |
| pYE2C-Mp-E465R | E465R | 81, 78 | 55 |
| pYE2C-Mp-E465L | E465L | 82, 78 | 111 |
| pYE2C-Mp-E465S | E465S | 83, 78 | 109 |
| pYE2C-Mp-E465T | E465T | 84, 78 | 107 |
| pYE2C-Mp-E465V | E465V | 85, 78 | 99 |
| pYE2C-Mp-E465W | E465W | 86, 78 | 108 |
| pYE2C-Mp-N469D | N469D | 87, 88 | 95 |
| pYE2C-Mp-N469Q | N469Q | 89, 88 | 99 |
| pYE2C-Mp-N469E | N469E | 90, 88 | 96 |
| pYE2C-Mp-D471N | D471N | 91, 92 | 109 |
| pYE2C-Mp-D471E | D471E | 93, 92 | 101 |
| pYE2C-Mp-D471Q | D471Q | 94, 92 | — |
| pYE2C-Mp-Q473E | Q473E | 95, 96 | 92 |
| pYE2C-Mp-Q473N | Q473N | 97, 96 | 99 |
| pYE2C-Mp-Q473D | Q473D | 98, 96 | 109 |
| pYE2C-Mp-N474D | N474D | 99, 100 | 94 |
| pYE2C-Mp-N474Q | N474Q | 101, 100 | 112 |
| pYE2C-Mp-N474E | N474E | 102, 100 | 98 |
| pYE2C-Mp-N475D | N475D | 103, 100 | 91 |
| pYE2C-Mp-N475Q | N475Q | 104, 100 | 98 |
| pYE2C-Mp-N475E | N475E | 105, 100 | 101 |

On the basis of Table 5, Xyl/Glc ratio (%) was determined to decrease by substituting glutamic acid at position 465 for aspartic acid, glutamic acid at position 465 for isoleucine or glutamic acid at position 465 for arginine in SEQ ID NO: 1.

In the case of substituting glutamic acid of SEQ ID NO: 1 for aspartic acid or substituting glutamic acid at position 465 for arginine in particular, Xyl/Glc ratio (%) decreased by 20% or more and the degree of improvement of substrate specificity was remarkable.

Moreover, in modified FAD-GDH obtained by substituting glutamic acid of SEQ ID NO: 1 for aspartic acid and substituting glutamic acid at position 465 for arginine, the values of the Mal/Glc ratio (%) were 79% and 72%, respectively, both the Mal/Glc ratio (%) and Xyl/Glc ratio (%) decreased by 20% or more, and substrate specificity was determined to be extremely high.

EXAMPLE 7

(Acquisition and Evaluation of Performance of FAD-GDH-expressing Yeast Introduced with Mutation for Improving Heat Resistance and Mutation for Improving Substrate Specificity)

The inventors of the present invention previously discovered that modified FAD-GDH obtained by substituting valine at position 232 for glutamic acid, threonine at position 387 for alanine and isoleucine at position 545 for threonine in SEQ ID NO: 1 have superior heat resistance. Therefore, it was decided to produce modified FAD-GDH having superior heat resistance and substrate specificity by causing various types of mutations for improving substrate specificity to accumulate in a triple mutant in which these three mutations for improving heat resistance were accumulated.

More specifically, site-specific mutations were sequentially introduced using recombinant plasmid pYE2C-Mp as template in compliance with Example 2 by using combinations of the synthetic nucleotides of SEQ ID NO: 106 and 107, SEQ ID NO: 108 and 109 and SEQ ID NO: 110 and 111 to produce recombinant plasmid YE2C-Mp-V232E/T387A/I545T encoding modified FAD-GDH obtained by substituting valine at position 232 for glutamic acid, threonine at position 387 for alanine and isoleucine at position 545 for threonine in SEQ ID NO: 1.

Next, recombinant plasmids encoding modified FAD-GDH introduced with target site-specific mutations were produced by using the recombinant plasmid pYE2C-Mp-V232E/T387A/I545T as template and using combinations of each of the synthetic nucleotides shown in Table 6 as primers. The produced modified forms are shown in Table 6. More specifically, these modified forms consisted of mutants obtained by substituting valine at position 232 for glutamic acid, threonine at position 387 for alanine and isoleucine at position 545 for threonine, and substituting leucine at position 121 for methionine, or, and tryptophan at position 569 for tyrosine, or, and serine at position 612 for cysteine or serine at position 612 for threonine, and recombinant plasmids containing genes encoding each of these mutations were designated pYE2C-Mp-V232E/T387A/I545T/L121M, pYE2C-Mp-V232E/T387A11545T/W569Y, pYE2C-Mp-V232E/T387A/I545T/S612C and pYE2C-Mp-V232E/T387A/I545T/S612T.

Moreover, recombinant plasmid pYE2C-Mp-V232E/T387A/E465D/I545T/W569Y encoding modified FAD-GDH obtained by substituting valine at position 232 for glutamic acid, threonine at position 387 for alanine, glutamic acid at position 465 for aspartic acid, isoleucine at position 545 for threonine and tryptophan at position 569 for tyrosine was produced by using recombinant plasmid pYE2C-Mp-V232E/T387A/I545T/W569Y as template and using combinations of the synthetic nucleotides of SEQ ID NO: 77 and 78 as primers.

Strain Inv-Sc was transformed in the same manner as Example 2 using the recombinant plasmids encoding modified Mucor-derived FAD-GDH introduced with site-specific mutations consisting of pYE2C-Mp-V232E/T387A/I545T/L121M, pYE2C-Mp-V232E/T387A/I545T/W569Y, pYE2C-Mp-V232E/T387A/I545T/S612C and pYE2C-Mp-V232E/T387A/I545T/S612T, pYE2C-Mp-V232E/T387A/E465D/I545T/W569Y, followed by culturing each of the transformants, confirming GHD activity in the culture supernatant, and measuring Xyl/Glc (%) and Xyl/Glc ratio (%) in the same manner as Example 2. The results are shown in Table 6.

Continuing, heat resistance of the modified FAD-GDH was evaluated using the same culture supernatant. More specifically, the evaluated FAD-GDH was diluted with enzyme diluent (10 mM acetate buffer, pH 5.0) to about 0.5 U/ml. Two aliquots of this enzyme solution (0.2 ml) were prepared, and one of the aliquots was stored at 4° C. while the other was subjected to heat treatment for 15 minutes at 60° C. Following heat treatment, the FAD-GDH activity of each sample was measured and the activity level after heat treatment for 15 minutes at 60° C. based on a value of 100 for the enzyme activity of the enzyme solution stored at 4° C. was calculated as "residual activity (%)". This residual activity (%) was used as an indicator for evaluating heat resistance of each modified FAD-GDH. The results are shown in Table 6.

TABLE 6

| Amino acid substitution site | | Primer sequence number | Residual activity (%) | Xyl/Glc (%) | Xyl/Glc ratio (%) |
|---|---|---|---|---|---|
| V232E/ T387A/ I545T | — | — | 18.2 | 2.0 | 100 |
| | L121M | 52, 51 | 0 | 2.4 | 121 |
| | W569Y | 70, 69 | 55.4 | 0.8 | 37 |
| | S612C | 73, 72 | 14.5 | 1.6 | 81 |
| | S612T | 74, 72 | 19.4 | 1.5 | 74 |
| | E465D/W569Y | 77, 78 | 49.6 | 0.4 | 19 |

As shown in Table 6, substrate specificity improved as a result of introducing W569Y, S612C or S612T into V232E/Y387A/I545T in comparison with prior to introduction. In addition, substrate specificity further improved as a result of introducing E465D into V232E/T387A/I545T/W569Y in comparison with prior to introduction. Moreover, heat resistance was determined to improve in modified FAD-GDH obtained by introducing W569Y into V232E/T387A/I545T in comparison with V232E/T387A/I545T.

Continuing, Mal/Glc ratio (%) was investigated in V232E/T387A/I545T/W569Y and V232E/T387A/E465D/I545T/W569Y. The Mal/Glc ratio (%) of V232E/T387A/I545T/W569Y was 34% and the Mal/Glc ratio (%) of V232E/T387A/E465D/I545T/W569Y was 40% based on a value of 100 for the Mal/Glc ratio (%) of V232E/T387A/I545T, and reactivity to maltose was also determined to decrease.

On the basis of these results, V232E/T387A/I545T/W569Y, V232E/T387A/I545T/S612C, V232E/T387A/I545T/S612T and V232E/T387A/E465D/I545T/W569Y were determined to have superior heat resistance and substrate specificity. In particular, V232E/T387A/I545T/W569Y and V232E/T387A/E465D/I545T/W569Y were determined to be extremely superior mutants since they further improved heat resistance in addition to decreasing reactivity to maltose and xylose by 20% or more in comparison with V232E/T387A/I545T.

As has been described above, since the FAD-GDH of the present invention demonstrates sufficiently high substrate specificity for D-glucose while also demonstrating sufficiently low reactivity to sugar compounds other than D-glucose such as D-xylose and maltose, D-glucose can be measured accurately even in cases of measuring D-glucose in a sample under conditions of containing large amounts of sugar compounds other than D-glucose or under conditions of a high enzyme concentration, and is expected to enable measurement with higher precision and higher sensitivity in comparison with the case of using conventional FAD-GDH in applications such as glucose sensors.

The invention claimed is:

1. A flavin-binding glucose dehydrogenase having the following amino acid substitutions in SEQ ID NO: 1 or amino acid sequence having a 90% or more sequence identity with the amino acid sequence of SEQ ID NO: 1:

the amino acid at the position corresponding to methionine at position 78 is selected from the group consisting of glutamic acid, glutamin, cysteine and asparagine, the amino acid at the position corresponding to tyrosine at position 79 is selected from the group consisting of phenylalanine and asparagine, the amino acid at the position corresponding to glutamine at position 81 is selected from the group consisting of leucine, phenylalanine and asparagine, the amino acid at the position corresponding to leucine at position 121 is selected from the group from the group consisting of cysteine and methionine, the amino acid at the position corresponding to valine at position 122 is selected from the group consisting of threonine, alanine and cysteine, the amino acid at the position corresponding to tryptophan at position 123 is selected from the group consisting of cysteine, phenylalanine, histidine, valine and serine, the amino acid at the position corresponding to glutamic acid at position 465 is selected from the group consisting of arginine and aspartic and, the amino acid at the position corresponding to tryptophan at position 569 is tyrosine, the amino acid at the position corresponding to serine at position 612 is selected from the group consisting of cysteine and threonine, the amino acid at the position corresponding to valine at position 232 in the amino acid sequence of SEQ ID NO: 1 is glutamic acid, the amino acid at the position corresponding to threonine at position 387 is alanine, the amino acid at the position corresponding to isoleucine at position 545 is threonine, and the amino acid at the position corresponding to tryptophan at position 569 is tyrosine, the amino acid at the position corresponding to valine at position 232 in the amino acid sequence of SEQ ID NO: 1 is glutamic acid, the amino acid at the position corresponding to threonine at position 387 is alanine, the amino acid at the position corresponding to isoleucine at position 545 is threonine, and the amino acid at the position corresponding to serine at position 612 is cysteine, the amino acid at the position corresponding to valine at position 232 in the amino acid sequence of SEQ ID NO: 1 is glutamic acid, the amino acid at the position corresponding to threonine at position 387 is alanine, the amino acid at the position corresponding to isoleucine at position 545 is threonine, and the amino acid at the position corresponding to serine at position 612 is threonine, the amino acid at the position corresponding to valine at position 232 in the amino acid sequence of SEQ ID NO: 1 is glutamic acid, the amino acid at the position corresponding to threonine at position 387 is alanine, the amino acid at the position corresponding to glutamic acid at position 465 is aspartic acid, the amino acid at the position corresponding to isoleucine at position 545 is threonine, and the amino acid at the position corresponding to tryptophan at position 569 is tyrosine, the amino acid at the position corresponding to tryptophan at position 569 is tyrosine and the amino acid at the position corresponding to methionine at position 78 is glutamic acid, the amino acid at the position corresponding to trytophan at position 569 is tyrosine and the amino acid at the position corresponding to methionine at position 78 is asparagine, the amino acid at the position corresponding to tryptophan at position 569 is tyrosine and the amino acid at the position corresponding to leucine at position 121 is methionine, the amino acid at the position corresponding to tryptophan at position 569 is tyrosine and the amino acid at the position corresponding to tryptophan at position 123 is phenylalanine, the amino acid at the position corresponding to tryptophan at position 569 is tyrosine and the amino acid at the position corresponding to tryptophan at position 123 is valine, the amino acid at the position corresponding to tryptophan at position 569 is tyrosine and the amino acid at the position corresponding to serine at position 612 is cysteine, or the amino acid at the position corresponding to tryptophan at position 569 is tyrosine and the amino acid at the position corresponding to serine at position 612 is threonine.

2. The flavin-binding glucose dehydrogenase according to claim 1, wherein the ratio of reactivity to D-xylose to reactivity to D-glucose (Xyl/Glc (%)) and/or the ratio of reactivity to maltose to reactivity to D-glucose (Mal/Glc (%)) is decreased by 20% or more in comparison with that prior to the introduction of the substitutions.

3. A flavin-binding glucose dehydrogenase gene encoding the flavin-binding glucose dehydrogenase according to claim 1.

4. A recombinant vector containing the flavin-binding glucose dehydrogenase gene according to claim 3.

5. A host cell containing the recombinant vector according to claim 3.

6. A method for producing a flavin-binding glucose dehydrogenase, comprising the following steps:
a step for culturing the host cell according to claim 5,
a step for expressing a flavin-binding glucose dehydrogenase gene contained in the host cells, and
a step for isolating the flavin-binding glucose dehydrogenase from the culture.

7. A method for measuring glucose using the flavin-binding glucose dehydrogenase according to claim 1.

8. A glucose assay kit containing the flavin-binding glucose dehydrogenase according to claim 1.

9. A glucose sensor containing the flavin-binding glucose dehydrogenase according to claim 1.

* * * * *

SEQUENCE LISTING

<160> NUMBER OF SEQ ID NOS: 111

<210> SEQ ID NO 1

```
<211> LENGTH: 641
<212> TYPE: PRT
<213> ORGANISM: Mucor prainii

<400> SEQUENCE: 1

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Ile Val Gly Gly Gly Val Ala Gly Leu Ala Leu Ala Ser
            35                  40                  45

Arg Ile Ser Glu Asn Lys Asp Val Thr Val Ala Val Leu Glu Ser Gly
50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
            115                 120                 125

Lys Asp Tyr Asp Ala Trp Glu Glu Leu Gly Asn Pro Gly Trp Asn Gly
130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
370                 375                 380

Ala Thr Thr Pro Asn Asn Leu Gly Tyr Pro Thr Pro Glu Gln Leu Phe
```

```
                385                 390                 395                 400
Asn Gly Thr Glu Phe Val Ser Gly Lys Glu Phe Ala Asp Lys Ile Arg
            405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
            435                 440                 445

Glu Glu Asn Tyr Leu Ser Pro Ile Glu Ile Asn Phe Thr Pro Gly Tyr
            450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
            515                 520                 525

Glu Ile Ile Thr Ala Ser Pro Gly Leu Gly Asp Ile Asn Ser Gly Glu
            530                 535                 540

Ile Glu Pro Gly Met Asn Ile Thr Ser Glu Asp Asp Leu Arg Ser Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
            595                 600                 605

Glu Val Ser Ser His Leu Met Gln Pro Thr Tyr Gly Ile Ala Glu Lys
            610                 615                 620

Ala Ala Asp Ile Ile Lys Asn Phe Tyr Lys Thr Gln His Lys Asn Gln
625                 630                 635                 640

Asn
```

<210> SEQ ID NO 2
<211> LENGTH: 1926
<212> TYPE: DNA
<213> ORGANISM: Mucor prainii

<400> SEQUENCE: 2

```
atgaagatca cagctgccat tatcactgtt gccacagcat ttgcttcttt tgcttctgct    60
caacaagaca caaattcttc ctcaactgat acttatgatt atgttatcgt tggcggcggt   120
gtagctggtt tggcttttggc tagtcgtatc tctgaaaaca aggatgtcac tgttgctgtt   180
ctcgagtccg gtcctaatgc aatgataga tttgttgttt atgctcctgg catgtatggc   240
caagctgttg gcactgatct ctgtcctctc attcctacta ctcctcaaga aaatatgggc   300
aacagaagtc tcacaatcgc tactggtaga ttgctcggtg gtggcagtgc tattaatggt   360
ctcgtttgga cccgtggtgg cttgaaggat tacgatgctt gggaggagct cggtaaccct   420
ggatggaacg gtgccaactt gttcaagtac tttaagaagg tcgaaaactt cactcctcct   480
actcctgccc aaattgaata cggcgctact tatcagaaaa gtgctcatgg caagaaggga   540
cctattgatg tctctttcac gaactacgag ttctctcaat ctgctagctg aacgcctca   600 ctcgaaaccc ttgatttcac tgcacttcct gatatcttga acggtacttt ggccggttac   660
```

```
tctaccactc caacatttt ggaccctgag actgttcaac gtgttgattc ctatactggt      720
tacattgctc cttacactag ccgtaacaac ctcaatgttt tggccaacca taccgtctcc      780
cgcattcaat ttgctcccaa gaatggtagc gaacctctca aggctaccgg tgttgaatgg      840
tatcccactg gcaacaagaa tcaaaagcaa attatcaagg cccgttatga agttatcatc      900
tcatctggtg ccattggtag tcctaagctt ttggaaatct ctggtatcgg taataaggat      960
atcgtctctg ctgctggtgt cgagtccttg attgacttgc ctggcgttgg ttccaacatg     1020
caagatcacg ttcatgctat cactgtctct actaccaata ttactggcta tactaccaac     1080
agcgtctttg tcaatgaaac ccttgcccaa gaacaaagag aagaatatga agccaacaag     1140
actggtatct gggctactac tcccaacaac ctcggttatc ctacgcccga caactcttc      1200 aatggcaccg aattcgtttc tggaaaggag tttgctgaca agattcgtaa ctctactgat     1260
gaatgggcca actattatgc ttccaccaac gcctccaatg tcgagttatt aaagaagcaa     1320
tatgctattg tcgcctctcg ttacgaagag aactacttgt ctcctattga aatcaacttc     1380
actcctggtt atgagggtag cggtaatgtc gatttgcaaa acaacaagta ccaaactgtc     1440
aaccatgtct tgattgctcc tttaagtcgt ggttatactc acattaactc ttctgatgtg     1500
gaggatcatt ctgtcattaa tccccaatac tactctcatc ctatggatat tgatgtccat     1560
atcgcttcca ctaaacttgc tcgcgaaatc atcactgcct ctcccggtct tggtgacatt     1620
aacagtggcg aaatcgaacc cggtatgaat attacttctg aagacgacct tagatcttgg     1680
ttgagtaata atgtccgttc tgactggcat cctgttggta cttgtgctat gcttcccaag     1740
gaattaggtg tgttgtcag ccccgctctc atggttacg gcacttccaa cttgcgtgtt      1800
gttgatgctt cgattatgcc cctcgaagtc tcttctcatt tgatgcaacc cacctacggt     1860
attgctgaga aggctgctga cattattaag aatttctaca agactcaaca caagaaccaa     1920
aattag                                                                1926

<210> SEQ ID NO 3
<211> LENGTH: 45
<212> TYPE: DNA
<213> ORGANISM: Artificial Sequence
<220> FEATURE:
<223> OTHER INFORMATION: Artificially Synthesized Primer Sequence

<400> SEQUENCE: 3
ggaatattaa gcttggtacc atgaagatca cagctgccat tatca                      45

<210> SEQ ID NO 4
<211> LENGTH: 48
<212> TYPE: DNA
<213> ORGANISM: Artificial Sequence
<220> FEATURE:
<223> OTHER INFORMATION: Artificially Synthesized Primer Sequence

<400> SEQUENCE: 4
gtggatccga gctcggtacc ctaattttgg ttcttgtgtt gagtcttg                   48

<210> SEQ ID NO 5
<211> LENGTH: 587
<212> TYPE: PRT
<213> ORGANISM: Penicillium amagasakiense

<400> SEQUENCE: 5

Tyr Leu Pro Ala Gln Gln Ile Asp Val Gln Ser Ser Leu Leu Ser Asp
1               5                   10                  15
```

```
Pro Ser Lys Val Ala Gly Lys Thr Tyr Asp Tyr Ile Ile Ala Gly Gly
            20                  25                  30

Gly Leu Thr Gly Leu Thr Val Ala Ala Lys Leu Thr Glu Asn Pro Lys
        35                  40                  45

Ile Lys Val Leu Val Ile Glu Lys Gly Phe Tyr Glu Ser Asn Asp Gly
    50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Arg Thr Asn
                85                  90                  95

Asn Ile Lys Ala Gly Lys Gly Leu Gly Gly Ser Thr Leu Ile Asn Gly
            100                 105                 110

Asp Ser Trp Thr Arg Pro Asp Lys Val Gln Ile Asp Ser Trp Glu Lys
        115                 120                 125

Val Phe Gly Met Glu Gly Trp Asn Trp Asp Asn Met Phe Glu Tyr Met
    130                 135                 140

Lys Lys Ala Glu Ala Ala Arg Thr Pro Thr Ala Ala Gln Leu Ala Ala
145                 150                 155                 160

Gly His Ser Phe Asn Ala Thr Cys His Gly Thr Asn Gly Thr Val Gln
                165                 170                 175

Ser Gly Ala Arg Asp Asn Gly Gln Pro Trp Ser Pro Ile Met Lys Ala
            180                 185                 190

Leu Met Asn Thr Val Ser Ala Leu Gly Val Pro Val Gln Gln Asp Phe
        195                 200                 205

Leu Cys Gly His Pro Arg Gly Val Ser Met Ile Met Asn Asn Leu Asp
    210                 215                 220

Glu Asn Gln Val Arg Val Asp Ala Ala Arg Ala Trp Leu Leu Pro Asn
225                 230                 235                 240

Tyr Gln Arg Ser Asn Leu Glu Ile Leu Thr Gly Gln Met Val Gly Lys
                245                 250                 255

Val Leu Phe Lys Gln Thr Ala Ser Gly Pro Gln Ala Val Gly Val Asn
            260                 265                 270

Phe Gly Thr Asn Lys Ala Val Asn Phe Asp Val Phe Ala Lys His Glu
        275                 280                 285

Val Leu Leu Ala Ala Gly Ser Ala Ile Ser Pro Leu Ile Leu Glu Tyr
    290                 295                 300

Ser Gly Ile Gly Leu Lys Ser Val Leu Asp Gln Ala Asn Val Thr Gln
305                 310                 315                 320

Leu Leu Asp Leu Pro Val Gly Ile Asn Met Gln Asp Gln Thr Thr Thr
                325                 330                 335

Thr Val Ser Ser Arg Ala Ser Ser Ala Gly Ala Gly Gln Gly Gln Ala
            340                 345                 350

Val Phe Phe Ala Asn Phe Thr Glu Thr Phe Gly Asp Tyr Ala Pro Gln
        355                 360                 365

Ala Arg Asp Leu Leu Asn Thr Lys Leu Asp Gln Trp Ala Glu Glu Thr
    370                 375                 380

Val Ala Arg Gly Gly Phe His Asn Val Thr Ala Leu Lys Val Gln Tyr
385                 390                 395                 400

Glu Asn Tyr Arg Asn Trp Leu Leu Asp Glu Asp Val Ala Phe Ala Glu
                405                 410                 415

Leu Phe Met Asp Thr Glu Gly Lys Ile Asn Phe Asp Leu Trp Asp Leu
            420                 425                 430

Ile Pro Phe Thr Arg Gly Ser Val His Ile Leu Ser Ser Asp Pro Tyr
```

```
                435                 440                 445
Leu Trp Gln Phe Ala Asn Asp Pro Lys Phe Phe Leu Asn Glu Phe Asp
    450                 455                 460
Leu Leu Gly Gln Ala Ala Ala Ser Lys Leu Ala Arg Asp Leu Thr Ser
465                 470                 475                 480
Gln Gly Ala Met Lys Glu Tyr Phe Ala Gly Glu Thr Leu Pro Gly Tyr
                485                 490                 495
Asn Leu Val Gln Asn Ala Thr Leu Ser Gln Trp Ser Asp Tyr Val Leu
            500                 505                 510
Gln Asn Phe Arg Pro Asn Trp His Ala Val Ser Ser Cys Ser Met Met
        515                 520                 525
Ser Arg Glu Leu Gly Gly Val Val Asp Ala Thr Ala Lys Val Tyr Gly
    530                 535                 540
Thr Gln Gly Leu Arg Val Ile Asp Gly Ser Ile Pro Pro Thr Gln Val
545                 550                 555                 560
Ser Ser His Val Met Thr Ile Phe Tyr Gly Met Ala Leu Lys Val Ala
                565                 570                 575
Asp Ala Ile Leu Asp Asp Tyr Ala Lys Ser Ala
            580                 585
```

<210> SEQ ID NO 6
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 6
gctcctggca tggctggcca agctgttggc         30

<210> SEQ ID NO 7
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 7
ggacagagat cagtgccaac agcttggcc          29

<210> SEQ ID NO 8
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 8
gctcctggca tggttggcca agctgttggc         30

<210> SEQ ID NO 9
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 9
gctcctggca tgcctggcca agctgttggc         30

<210> SEQ ID NO 10

```
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 10
gctcctggca tgtgtggcca agctgttggc                                              30

<210> SEQ ID NO 11
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 11
gctcctggca tgaatggcca agctgttggc                                              30

<210> SEQ ID NO 12
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 12
gctcctggca tgcaaggcca agctgttggc                                              30

<210> SEQ ID NO 13
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 13
gctcctggca tgtctggcca agctgttggc                                              30

<210> SEQ ID NO 14
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 14
gctcctggca tgactggcca agctgttggc                                              30

<210> SEQ ID NO 15
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 15
gctcctggca tgcatggcca agctgttggc                                              30

<210> SEQ ID NO 16
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 16
```
gctcctggca tgtttggcca agctgttggc                                          30

<210> SEQ ID NO 17
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 17
gctcctggca tgtggggcca agctgttggc                                          30

<210> SEQ ID NO 18
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 18
gctcctggca tgaagggcca agctgttggc                                          30

<210> SEQ ID NO 19
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 19
agtgctatta atcatctcgt ttggacccgt                                          30

<210> SEQ ID NO 20
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 20
atccttcaag ccaccacggg tccaaacgag                                          30

<210> SEQ ID NO 21
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 21
agtgctatta attgtctcgt ttggacccgt                                          30

<210> SEQ ID NO 22
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 22
agtgctatta atgagctcgt ttggacccgt                                          30

<210> SEQ ID NO 23
<211> LENGTH: 30
<212> TYPE: DNA

```
<213> ORGANISM: Artificial Sequence
<220> FEATURE:
<223> OTHER INFORMATION: Artificially Synthesized Primer Sequence

<400> SEQUENCE: 23
agtgctatta ataagctcgt tggacccgt                                30

<210> SEQ ID NO 24
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 24
agtgctatta attggctcgt ttggacccgt                               30

<210> SEQ ID NO 25
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 25
agtgctatta atatgctcgt ttggacccgt                               30

<210> SEQ ID NO 26
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 26
agtaataatg tccattctga ctggcatcct                               30

<210> SEQ ID NO 27
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 27
gcacaagtac caacaggatg ccagtcaga                                29

<210> SEQ ID NO 28
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 28
agtaataatg tcatgtctga ctggcatcct                               30

<210> SEQ ID NO 29
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 29
agtaataatg tctattctga ctggcatcct                               30
```

<210> SEQ ID NO 30
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 30
agtaataatg tccaatctga ctggcatcct                              30

<210> SEQ ID NO 31
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 31
agtaataatg tcgagtctga ctggcatcct                              30

<210> SEQ ID NO 32
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 32
agtaataatg tcaagtctga ctggcatcct                              30

<210> SEQ ID NO 33
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 33
gaagtctctt ctaagttgat gcaacccacc                              30

<210> SEQ ID NO 34
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 34
ctcagcaata ccgtaggtgg gttgcatcaa                              30

<210> SEQ ID NO 35
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 35
gaagtctctt ctcgtttgat gcaacccacc                              30

<210> SEQ ID NO 36
<211> LENGTH: 30
<212> TYPE: DNA
<213> ORGANISM: Artificial Sequence
<220> FEATURE:

<223> OTHER INFORMATION: Artificially Synthesized Primer Sequence

<400> SEQUENCE: 36
gaagtctctt ctaatttgat gcaacccacc                                    30

<210> SEQ ID NO 37
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 37
gaagtctctt ctgatttgat gcaacccacc                                    30

<210> SEQ ID NO 38
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 38
gtttatgctc ctgccatgta tggccaagct                                    30

<210> SEQ ID NO 39
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 39
gagatcagtg ccaacagctt ggccatacat                                    30

<210> SEQ ID NO 40
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 40
tatgctcctg gctgttatgg ccaagctgtt                                    30

<210> SEQ ID NO 41
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 41
acagagatca gtgccaacag cttggccata                                    30

<210> SEQ ID NO 42
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 42
tatgctcctg gcgactatgg ccaagctgtt                                    30

```
<210> SEQ ID NO 43
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 43
tatgctcctg gcaattatgg ccaagctgtt                                    30

<210> SEQ ID NO 44
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 44
tatgctcctg gcgagtatgg ccaagctgtt                                    30

<210> SEQ ID NO 45
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 45
tatgctcctg gccagtatgg ccaagctgtt                                    30

<210> SEQ ID NO 46
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 46
ggcatgtatg gcctagctgt tggcactgat                                    30

<210> SEQ ID NO 47
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 47
aatgagagga cagagatcag tgccaacagc                                    30

<210> SEQ ID NO 48
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 48
ggcatgtatg gcttcgctgt tggcactgat                                    30

<210> SEQ ID NO 49
<211> LENGTH: 30
<212> TYPE: DNA
<213> ORGANISM: Artificial Sequence
<220> FEATURE:
<223> OTHER INFORMATION: Artificially Synthesized Primer Sequence
```

<400> SEQUENCE: 49
ggcatgtatg gcaatgctgt tggcactgat                                    30

<210> SEQ ID NO 50
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 50
gctattaatg gttgcgtttg gacccgtggt                                    30

<210> SEQ ID NO 51
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 51
gtaatccttc aagccaccac gggtccaaac                                    30

<210> SEQ ID NO 52
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 52
gctattaatg gtatggtttg gacccgtggt                                    30

<210> SEQ ID NO 53
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 53
attaatggtc tcacttggac ccgtggtggc                                    30

<210> SEQ ID NO 54
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 54
cgtaatcctt caagccacca cgggtcca                                      28

<210> SEQ ID NO 55
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 55
attaatggtc tcatttggac ccgtggtggc                                    30

<210> SEQ ID NO 56
<211> LENGTH: 30

```
<212> TYPE: DNA
<213> ORGANISM: Artificial Sequence
<220> FEATURE:
<223> OTHER INFORMATION: Artificially Synthesized Primer Sequence

<400> SEQUENCE: 56
attaatggtc tcgcttggac ccgtggtggc                                           30

<210> SEQ ID NO 57
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 57
attaatggtc tcatgtggac ccgtggtggc                                           30

<210> SEQ ID NO 58
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 58
attaatggtc tctgttggac ccgtggtggc                                           30

<210> SEQ ID NO 59
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 59
aatggtctcg tttgtacccg tggtggcttg                                           30

<210> SEQ ID NO 60
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 60
agcatcgtaa tccttcaagc caccacgggt                                           30

<210> SEQ ID NO 61
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 61
aatggtctcg tttttacccg tggtggcttg                                           30

<210> SEQ ID NO 62
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 62
```
aatggtctcg ttcatacccg tggtggcttg          30

<210> SEQ ID NO 63
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 63
aatggtctcg ttgtgacccg tggtggcttg          30

<210> SEQ ID NO 64
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 64
aatggtctcg tttcgacccg tggtggcttg          30

<210> SEQ ID NO 65
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 65
aatgtccgtt ctaactggca tcctgttggt          30

<210> SEQ ID NO 66
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 66
gcatagcaca agtaccaaca ggatgcca          28

<210> SEQ ID NO 67
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 67
aatgtccgtt ctgagtggca tcctgttggt          30

<210> SEQ ID NO 68
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 68
gtccgttctg acttccatcc tgttggtact          30

<210> SEQ ID NO 69
<211> LENGTH: 30
<212> TYPE: DNA
<213> ORGANISM: Artificial Sequence

```
<220> FEATURE:
<223> OTHER INFORMATION: Artificially Synthesized Primer Sequence

<400> SEQUENCE: 69
gggaagcata gcacaagtac caacaggatg                                          30

<210> SEQ ID NO 70
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 70
gtccgttctg actatcatcc tgttggtact                                          30

<210> SEQ ID NO 71
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 71
ctcgaagtct ctgctcattt gatgcaaccc                                          30

<210> SEQ ID NO 72
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 72
gcaataccgt aggtgggttg catcaaatg                                           29

<210> SEQ ID NO 73
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 73
ctcgaagtct cttgtcattt gatgcaaccc                                          30

<210> SEQ ID NO 74
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 74
ctcgaagtct ctactcattt gatgcaaccc                                          30

<210> SEQ ID NO 75
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 75
aatggtatgg tttttacccg tggtggcttg                                          30
```

<210> SEQ ID NO 76
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 76
aatggtatgg ttgtgacccg tggtggcttg                              30

<210> SEQ ID NO 77
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 77
actcctggtt atgatggtag cggtaatgtc                              30

<210> SEQ ID NO 78
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 78
gttgttttgc aaatcgacat taccgctacc                              30

<210> SEQ ID NO 79
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 79
actcctggtt atggtggtag cggtaatgtc                              30

<210> SEQ ID NO 80
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 80
actcctggtt atattggtag cggtaatgtc                              30

<210> SEQ ID NO 81
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 81
actcctggtt atcgtggtag cggtaatgtc                              30

<210> SEQ ID NO 82
<211> LENGTH: 30
<212> TYPE: DNA
<213> ORGANISM: Artificial Sequence
<220> FEATURE:
<223> OTHER INFORMATION: Artificially Synthesized Primer Sequence

```
<400> SEQUENCE: 82
actcctggtt atctgggtag cggtaatgtc                                    30

<210> SEQ ID NO 83
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 83
actcctggtt attcgggtag cggtaatgtc                                    30

<210> SEQ ID NO 84
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 84
actcctggtt atacgggtag cggtaatgtc                                    30

<210> SEQ ID NO 85
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 85
actcctggtt atgtgggtag cggtaatgtc                                    30

<210> SEQ ID NO 86
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 86
actcctggtt attggggtag cggtaatgtc                                    30

<210> SEQ ID NO 87
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 87
gagggtagcg gtgatgtcga tttgcaaaac                                    30

<210> SEQ ID NO 88
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 88
agtttggtac ttgttgtttt gcaaatcgac                                    30

<210> SEQ ID NO 89
```

<210> SEQ ID NO 89
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 89
gagggtagcg gtcaggtcga tttgcaaaac                                   30

<210> SEQ ID NO 90
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 90
gagggtagcg gtgaggtcga tttgcaaaac                                   30

<210> SEQ ID NO 91
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 91
agcggtaatg tcaatttgca aaacaacaag                                   30

<210> SEQ ID NO 92
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 92
gttgacagtt tggtacttgt tgttttgcaa                                   30

<210> SEQ ID NO 93
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 93
agcggtaatg tcgagttgca aaacaacaag                                   30

<210> SEQ ID NO 94
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 94
agcggtaatg tccagttgca aaacaacaag                                   30

<210> SEQ ID NO 95
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 95

```
aatgtcgatt tggaaaacaa caagtaccaa                                          30
```

<210> SEQ ID NO 96
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 96

```
gacatggttg acagtttggt acttgttgtt                                          30
```

<210> SEQ ID NO 97
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 97

```
aatgtcgatt tgaataacaa caagtaccaa                                          30
```

<210> SEQ ID NO 98
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 98

```
aatgtcgatt tggataacaa caagtaccaa                                          30
```

<210> SEQ ID NO 99
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 99

```
gatttgcaag acaacaagta ccaaactgtc                                          30
```

<210> SEQ ID NO 100
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 100

```
aatcaagaca tggttgacag tttggtactt                                          30
```

<210> SEQ ID NO 101
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 101

```
gatttgcaac agaacaagta ccaaactgtc                                          30
```

<210> SEQ ID NO 102
<211> LENGTH: 30
<212> TYPE: DNA

<213> ORGANISM: Artificial Sequence
<220> FEATURE:
<223> OTHER INFORMATION: Artificially Synthesized Primer Sequence

<400> SEQUENCE: 102
gatttgcaag agaacaagta ccaaactgtc                                    30

<210> SEQ ID NO 103
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 103
gatttgcaaa acgacaagta ccaaactgtc                                    30

<210> SEQ ID NO 104
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 104
gatttgcaaa accagaagta ccaaactgtc                                    30

<210> SEQ ID NO 105
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 105
gatttgcaaa acgagaagta ccaaactgtc                                    30

<210> SEQ ID NO 106
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 106
gaccctgaga ctgagcaacg tgttgattcc                                    30

<210> SEQ ID NO 107
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 107
aatgtaacca gtataggaat caacacgttg                                    30

<210> SEQ ID NO 108
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 108
atctgggcta ctgctcccaa caacctcggt                                    30

```
<210> SEQ ID NO 109
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 109
ttcgggcgta ggataaccga ggttgttggg                                      30

<210> SEQ ID NO 110
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 110
aacagtggcg aaaccgaacc cggtatgaat                                      30

<210> SEQ ID NO 111
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 111
gtcttcagaa gtaatattca taccgggttc                                      30
```